(12) United States Patent
Sunagawa

(10) Patent No.: US 6,334,849 B1
(45) Date of Patent: Jan. 1, 2002

(54) HEART-FUNCTION MONITOR APPARATUS

(75) Inventor: Kenji Sunagawa, Ibaraki (JP)

(73) Assignee: Colin Corporation, Aichi-ken (JP)

( * ) Notice: Subject to any disclaimer, the term of this patent is extended or adjusted under 35 U.S.C. 154(b) by 0 days.

(21) Appl. No.: 09/576,435

(22) Filed: May 22, 2000

(30) Foreign Application Priority Data

May 25, 1999 (JP) .......................................... 11-145503

(51) Int. Cl.$^7$ ................................................. A61B 5/02
(52) U.S. Cl. ........................ 600/485; 600/500; 600/508
(58) Field of Search ................................ 600/500, 490, 600/485, 526, 504, 561, 586, 508, 503

(56) References Cited

U.S. PATENT DOCUMENTS 5,921,936 A * 7/1999 Inukai et al. ............... 600/490
6,090,047 A 7/2000 Kass et al.

OTHER PUBLICATIONS

Senzaki, Hideaki et al., "Single–Beat Estimation of End–Systolic Pressure–Volume Relation in Humans", *Circulation*, vol. 94, No. 10 (Nov. 15, 1996), pp. 2497–2506 (http://circ.ahajournals.org/cgi/content/full/94/10/2497 (Mar. 6, 2001), pp. 1–19).

* cited by examiner

*Primary Examiner*—Eric F. Winakur
*Assistant Examiner*—Navin Natnithithadha
(74) *Attorney, Agent, or Firm*—Oliff & Berridge, PLC

(57) ABSTRACT

An apparatus for monitoring a function of the heart of a person, including a pre-ejection period measuring device which non-invasively measures a pre-ejection period, an ejection-period measuring device which non-invasively measures an ejection period, an aorta-pressure estimating device for estimating blood pressure values in the aorta, a telediastolic-aorta-pressure determining device for determining, based on the estimated aorta blood pressure values, a telediastolic blood pressure in the aorta at a telediastolic time of the heart, a telesystolic-aorta-pressure determining device for determining, based on the estimated aorta blood pressure values, a telesystolic blood pressure in the aorta at a telesystolic time of the heart, an stroke-volume measuring device which non-invasively measures a stroke volume of the left ventricle, and a telesystolic-elastance determining device for determining, based on the measured pre-ejection period, ejection period, and stroke volume and the determined aorta telediastolic and telesystolic blood pressure values, a telesystolic elastance of the left ventricle, according a predetermined relationship between (A) left-ventricle telesystolic elastance and (B) (b1) pre-ejection period, (b2) ejection period, (b3) aorta telediastolic blood pressure, (b4) aorta telesystolic blood pressure, and (b5) stroke volume.

25 Claims, 11 Drawing Sheets

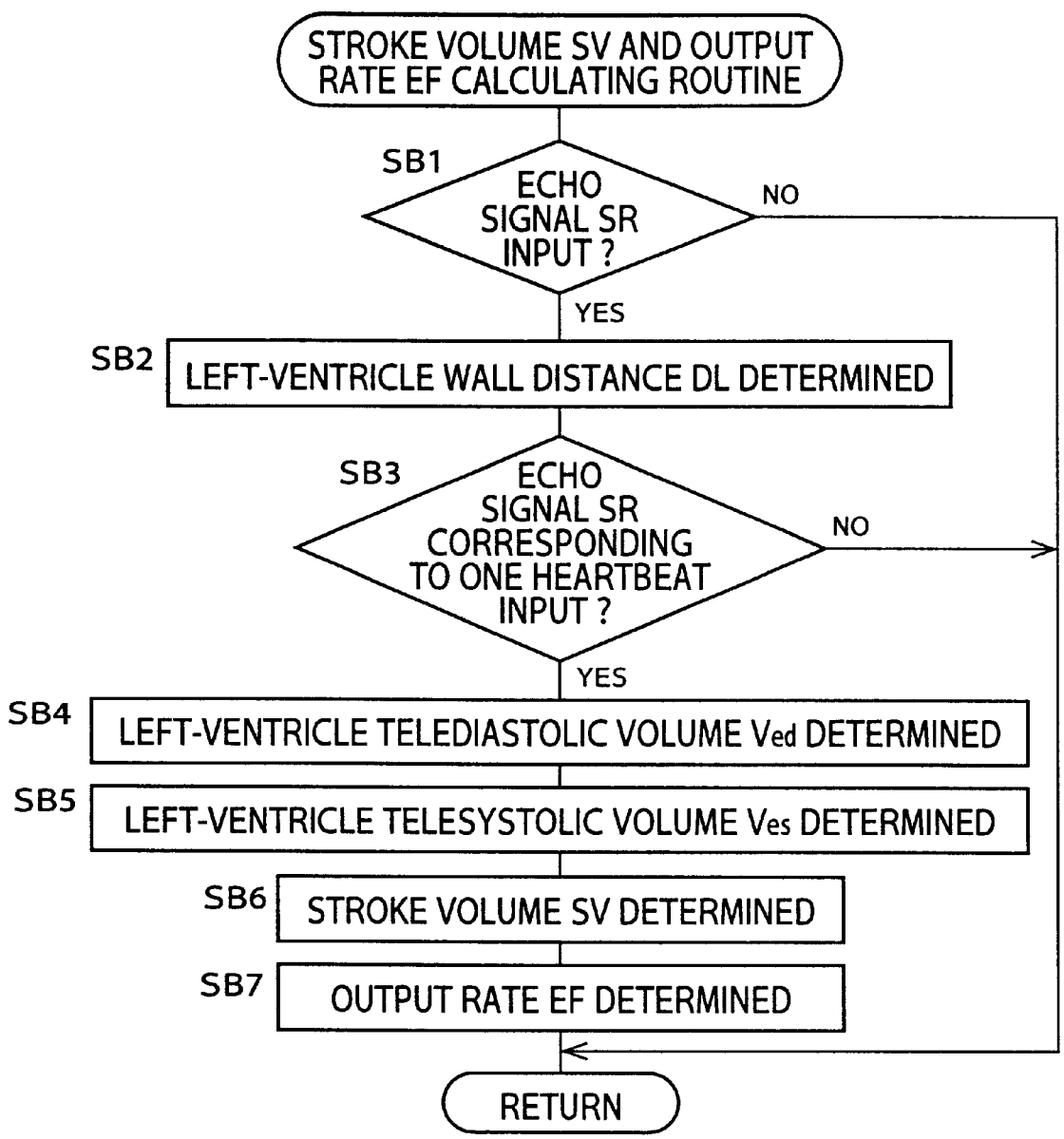

HEART-FUNCTION MONITOR APPARATUS

BACKGROUND OF THE INVENTION

1. Field of the Invention

The present invention relates to a heart-function monitor apparatus which monitors a function of the heart of a living subject by evaluating a blood-outputting ability of the left ventricle of the heart.

2. Related Art Statement

When a characteristic of the left ventricle of the heart as an elastic tube, that is, an elastic coefficient of the same, at a telesystolic time immediately before the aortic valve is closed, is defined as a left-ventricle telesystolic elastance $E_{es}$, the elastance $E_{es}$ indicates a blood-outputting ability of the left ventricle. Accordingly, the elastance $E_{es}$ can be used as an important index of the function of the heart. For example, the elastance $E_{es}$ can be used as a quantitative index of the dynamic condition of the circulatory system of a patient under intensive care or anesthesia.

However, determination of the above left-ventricle telesystolic elastance $E_{es}$, which is also known as the maximum pressure-volume ratio, or the left-ventricle telesystolic pressure-volume ratio, needs (a) detecting continuously respective changes of the inner pressure and inner volume of the left ventricle, (h) obtaining, in a two-dimensional coordinate system having a volume axis indicative of the inner volume of the left ventricle and a pressure axis indicative of the inner pressure of the same, a plurality of pressure-volume loops before and after preload or afterload is applied to the cardiac muscle, (c) estimating, based on the plurality of pressure-volume loops, a left-ventricle unstressed volume, $V_0$, taken when the inner pressure would take zero, and (d) determining the telesystolic elastance $E_{es}$ by dividing a telesystolic pressure, $P_{es}$, by the difference of a telesystolic volume, $V_{es}$, and the unstressed volume $V_0$. Thus, the determination of the telesystolic elastance $E_{es}$ needs measuring simultaneously the inner pressure and inner volume of the left ventricle. Conventionally, this determination has been carried out by an invasive method in which a cutting operation or a catheter insertion is needed. Thus, it has been very difficult to monitor the cardiac function.

SUMMARY OF THE INVENTION

It is therefore an object of the present invention to provide a heart-function monitor apparatus which can non-invasively and easily monitor a left-ventricle telesystolic elastance $E_{es}$ of a living subject.

The Inventor has carried out extensive studies in the above-mentioned background, and has found the fact that when (a) a pressure-volume ratio, E(t), is obtained by dividing a continuously obtained left-ventricle inner pressure, P(t), by the difference, $(V(t)-V_0)$, of a continuously obtained left-ventricle inner volume, V(t), and the above-indicated unstressed volume $V_0$, (b) a time-and-pressure-volume-ratio curve is drawn, as shown in FIG. 8, in a two-dimensional coordinate system having a time axis and a pressure-volume-ratio axis, (c) a first portion of a length of the time-and-pressure-volume-ratio curve between its start end and a maximum pressure-volume ratio, $E_{max}$, i.e., a left-ventricle telesystolic elastance $E_{es}$ (the first portion corresponds to a pre-ejection period, PEP) is approximated by a straight line, $L_1$, and a second portion of the length (the second portion corresponds to an ejection period, ET) is approximated by a straight line, $L_2$, and (d) $\alpha_0$ is defined as being equal to the ratio, $\alpha_2/\alpha_1$, of a slope, $\alpha_2$, of the straight line $L_2$ to a slope, $\alpha_1$, of the straight line $L_1$, the left-ventricle telesystolic elastance $E_{es}$ can be expressed by using a telediastolic aorta (blood) pressure, $P_{ad}$, i.e., an aorta inner pressure at a telediastolic time of the heart; a telesystolic aorta pressure $P_{es}$, i.e., an aorta inner pressure at a telesystolic time of the heart; the ejection period ET and the pre-ejection period PEP of the left ventricle; a stroke volume, SV, i.e., a volume of the blood outputted by one beat of the left ventricle; a telediastolic left-ventricle pressure, $P_{ed}$, i.e., a left-ventricle inner pressure at the telediastolic time of the heart; and the ratio $\alpha_0$. The present invention has been developed based on this finding.

(1) According to a first feature of the present invention, there is provided an apparatus for monitoring a function of a heart of a living subject, comprising a pre-ejection period measuring device which non-invasively measures a pre-ejection period from a time when contraction of a cardiac muscle of a left ventricle of the heart starts, to a time when ejection of blood from the left ventricle starts; an ejection-period measuring device which non-invasively measures an ejection period during which the blood is ejected from the left ventricle; an aorta-pressure estimating means for estimating blood pressure values in an aorta of the subject; a telediastolic-aorta-pressure determining means for determining, based on the aorta blood pressure values estimated by the aorta-pressure estimating means, a telediastolic blood pressure in the aorta at a telediastolic time of the heart; a telesystolic-aorta-pressure determining means for determining, based on the aorta blood pressure values estimated by the aorta-pressure estimating means, a telesystolic blood pressure in the aorta at a telesystolic time of the heart; a stroke-volume measuring device which non-invasively measures a stroke volume that is a volume of blood ejected from the left ventricle of the heart by a one-time beat of the heart; and a telesystolic-elastance determining means for determining, based on the measured pre-ejection period, the measured ejection period, the determined aorta telediastolic blood pressure, the determined aorta telesystolic blood pressure, and the measured stroke volume, a telesystolic elastance of the left ventricle of the heart, according to a predetermined relationship between (A) left-ventricle telesystolic elastance and (B) (b1) pre-ejection period, (b2) ejection period, (b3) aorta telediastolic blood pressure, (b4) aorta telesystolic blood pressure, and (b5) stroke volume.

According to this feature, the telesystolic-elastance determining means determines, based on the pre-ejection period, the ejection period, the telediastolic aorta blood pressure, the telesystolic aorta blood pressure, and the stroke volume all of which are non-invasively measured or determined, a telesystolic (i.e., end-systolic) elastance of the left ventricle of the heart of the subject, according the predetermined relationship. Thus, the present heart-function monitor apparatus can non-invasively and easily monitor the left ventricular end-systolic elastance corresponding to the cardiac function of the subject.

(2) According to a second feature of the present invention that includes the first feature (1), the telesystolic-elastance determining means comprises means for determining, according the predetermined relationship, the telesystolic elastance of the left ventricle of the heart, based on the measured pre-ejection period, the measured ejection period, the determined aorta telediastolic blood pressure, the determined aorta telesystolic blood pressure, the measured stroke volume, and a predetermined telediastolic (i.e., end-diastolic) pressure in the left ventricle at the telediastolic time of the heart. The left ventricular end-diastolic pressure is, e.g., 10 mmHg, but may be non-invasively estimated by the present monitor apparatus.

(3) According to a third feature of the present invention that includes the second feature (2), the predetermined relationship is defined by a following expression:

$$E_{es}=[P_{ad}+\{(P_{ad}-P_{ed})/PEP\}\times ET\times\alpha_0-P_{es}]/SV$$

where $E_{es}$ is the left-ventricle telesystolic elastance, $P_{ad}$ is the aorta telediastolic blood pressure, $P_{es}$ is the aorta telesystolic blood pressure, $P_{ed}$ is the left-ventricle telediastolic pressure, ET is the ejection period, PEP is the pre-ejection period, SV is the stroke volume, and $\alpha_0$ is a coefficient.

The above expression is obtained based on the fact that when a portion of the time-elastance curve (FIG. 8) between its start end and the maximum elastance $E_{max}$, i.e., the telesystolic elastance $E_{es}$ is approximated by the two straight lines $L_1$, $L_2$, the elastance $E_{es}$ can be expressed by using the telediastolic aorta (blood) pressure $P_{ad}$, the telesystolic aorta pressure $P_{es}$, the ejection period ET, the pre-ejection period PEP, the stroke volume SV, the telediastolic left-ventricle pressure, and the ratio $\alpha_0$ of the slope $\alpha_2$ of the line $L_2$ to the slope $\alpha_1$ of the line $L_1$.

(4) According to a fourth feature of the present invention that includes the third feature (3), the monitor apparatus further comprises an output-rate measuring device which non-invasively measures a volume of the left ventricle at the telediastolic time of the heart, and determines an output rate of the left ventricle of the heart by dividing the measured stroke volume by the measured left-ventricle telediastolic volume, and the telesystolic-elastance determining means determines, based on the measured pre-ejection period, the measured ejection period, the determined aorta telediastolic blood pressure, the determined aorta telesystolic blood pressure, the measured stroke volume, the measured output rate, and the left-ventricle telediastolic pressure, a telesystolic elastance of the left ventricle of the heart, according a predetermined relationship between) (A) left-ventricle telesystolic elastance and (B) (b1) pre-ejection period, (b2) ejection period, (b3) aorta telediastolic blood pressure, (b4) aorta telesystolic blood pressure, (b5) stroke volume, and (b6) output rate. According to this feature, the output-rate measuring device measures the output rate (i.e., ejection fraction) of the left ventricle that is known as being well correlated to the telesystolic elastance, and the telesystolic-elastance determining means determines the telesystolic elastance of the left ventricle, based on the measured output rate, the measured pre-ejection period, the measured ejection period, the determined aorta telediastolic blood pressure, the determined aorta telesystolic blood pressure, the measured stroke volume, the measured output rate, and the left-ventricle telediastolic pressure. Thus, the telesystolic-elastance determining means determines a more accurate telesystolic elastance of the left ventricle.

(5) According to a fifth feature of the present invention that includes the fourth feature (4), the coefficient $\alpha_0$ of the expression is defined by a following expression:

$$\alpha_0=C_1+C_2\times EXP(C_3\times EF)$$

where

EF is the measured output rate, $C_1$, $C_2$, and $C_3$ are constants which are experimentally obtained, and EXP(Z) is an exponential function of Z.

(6) According to a sixth feature of the present invention that includes of the fourth feature (4), the coefficient $\alpha_0$ of the expression is defined by a following expression:

$$\alpha_0=C_1+C_2\times EXP(C_3\times EF)+C_4\times EXP\{C_5\times PEP/(PEP+ET)\}$$

where

EF is the measured output rate, $C_1$, $C_2$, $C_3$, $C_4$, and $C_5$ are constants which are experimentally obtained, and EXP(Z) is an exponential function of Z.

According to this expression, the coefficient $\alpha_0$ occurring to the expression used according to the third feature (3) is determined based on the measured output rate and a ventricular contraction index, $I_V$ (=PEP/(PEP+ET)), that is conventionally known as an index of cardiac contractility. Therefore, the telesystolic-elastance determining means can more accurately determine the left ventricular telesystolic elastance according to the expression used according to the third feature (3).

(7) According to a seventh feature of the present invention that includes any of the first to sixth features (1) to (6), the pre-ejection period measuring device comprises an electrocardiograph which includes a plurality of electrodes adapted to contact a body surface of the subject, and which detects, from the subject, an electrocardiogram waveform including a Q wave; a heart-sound detecting device which is located in a body cavity of the subject, at a position in a vicinity of the heart of the subject, and which detects, from the subject, at least a first heart sound I; and means for determining, as the pre-ejection period, a time period from a time when the Q wave of the electrocardiogram waveform is detected to a time when an end of the first heart sound I is detected. Thus, the pre-ejection period measuring device can non-invasively measure the pre-ejection period PEP with accuracy.

(8) According to an eighth feature of the present invention that includes any one of the first to seventh features (1) to (7), the ejection-period measuring device comprises a heart-sound detecting device which is worn on the subject, at a position in a vicinity of the heart of the subject, and which detects, from the subject, a first heart sound I and a second heart sound II; and means for determining, as the ejection period, a time period from a time when an end of the first heart sound I is detected to a time when a start of the second heart sound II is detected. The ejection-period measuring device can non-invasively measure the ejection period ET with accuracy.

(9) According to a ninth feature of the present invention that includes any one of the first to eighth features (1) to (8), the telediastolic-aorta-pressure determining means comprises an electrocardiograph which includes a plurality of electrodes adapted to contact a body surface of the subject, and which detects, from the subject, an electrocardiogram waveform including a Q wave; and means for determining, as the telediastolic aorta blood pressure, a blood pressure which is estimated by the aorta-pressure estimating means as an aorta blood pressure at a time when the Q wave of the electrocardiogram waveform is detected by the electrocardiograph. The telediastolic-aorta-pressure determining means can non-invasively determine the telediastolic aorta blood pressure with accuracy.

(10) According to a tenth feature of the present invention that includes any one of the first to ninth features (1) to (9), the telesystolic-aorta-pressure determining means comprises a heart-sound detecting device which is worn on the subject, at a position in a vicinity of the heart of the subject, and which detects at least a second heart sound II from the subject; and means for determining, as the telesystolic aorta blood pressure, a blood pressure which is estimated by the aorta-pressure estimating means as an aorta blood pressure at a time when a start of the second heart sound II is detected by the heart-sound detecting device. The telesystolic-aorta-pressure determining means can non-invasively determine the telesystolic aorta blood pressure with accuracy.

(11) According to an eleventh feature of the present invention that includes any one of the first to tenth features (1) to (10), the pre-ejection period measuring device non-invasively measures, each time the heart contracts and expands, a pre-ejection period from a time when the contraction of the cardiac muscle of the left ventricle of the heart starts, to a time when the ejection of the blood from the left ventricle starts; the ejection period measuring device non-invasively measures, each time the heart contracts and expands, an ejection period during which the blood is ejected from the left ventricle starts; the aorta-pressure estimating means estimates, each time the heart contracts and expands, blood pressure values in the aorta of the subject; each time the heart contracts and expands, the telediastolic-aorta-pressure determining means determines, based on the estimated blood pressure values of the aorta, a telediastolic blood pressure in the aorta at a telediastolic time of the heart; each time the heart contracts and expands, the telesystolic-aorta-pressure determining means determines, based on the estimated blood pressure values of the aorta, a telesystolic blood pressure in the aorta at a telesystolic time of the heart; each time the heart contracts and expands, the stroke-volume measuring device measures a stroke volume of the left ventricle; and each time the heart contracts and expands, the telesystolic elastance determining means determines, based on the measured pre-ejection period, the measured ejection period, the determined telediastolic aorta blood pressure, the determined telesystolic aorta blood pressure, and the measured stroke volume, a telesystolic elastance value of the left ventricle of the heart according to said predetermined relationship, and the monitor apparatus further comprises a display device which displays, along an axis indicative of time, the left-ventricle telesystolic elastance values which are successively determined by the telesystolic elastance determining means as the heart successively contracts and expands. According to this feature, since the display device displays a timewise trend of the successively determined left ventricular end-systolic elastance values, a doctor or a nurse, for example, can recognize, when the cardiac function of a patient who is undergoing a surgical operation is lowering, the tendency or direction of change of the cardiac function, from the displayed timewise trend. Therefore, the doctor or nurse can estimate an abnormality of the cardiac function before the cardiac function actually indicates the abnormality.

(12) According to a twelfth feature of the present invention that includes any one of the first to eleventh features (1) to (11), the aorta-pressure estimating means comprises a blood-pressure measuring device which includes an inflatable cuff adapted to be wound around a body portion of the subject, and which measures at least one blood pressure of the subject when an air pressure in the cuff is changed; a pulse-wave sensor which is adapted to be pressed against an artery of the subject via a skin tissue of the subject so as to flatten a portion of a wall of the artery, and which detects a pressure pulse wave transmitted thereto from the artery via the flattened wall portion of the artery and the skin tissue; relationship determining means for determining a relationship between blood pressure and pressure-pulse-wave magnitude, based on at least one blood pressure measured by the blood-pressure measuring device and at least one magnitude of the pressure pulse wave detected by the pulse-wave sensor; and means for calibrating, according to the determined relationship, instantaneous magnitudes of the pressure pulse wave detected by the pulse-wave sensor, and thereby providing a waveform representing the estimated aorta blood pressure values of the subject.

BRIEF DESCRIPTION OF THE DRAWINGS

The above and optional objects, features and advantages of the present invention will be better understood by reading the following detailed description of the preferred embodiments of the invention when considered in conjunction with the accompanying drawings, in which:

FIG. 11 is a flow chart representing a stroke-volume and output-rate calculating routine of the control program.

DETAILED DESCRIPTION OF THE PREFERRED EMBODIMENTS

Figure 1:
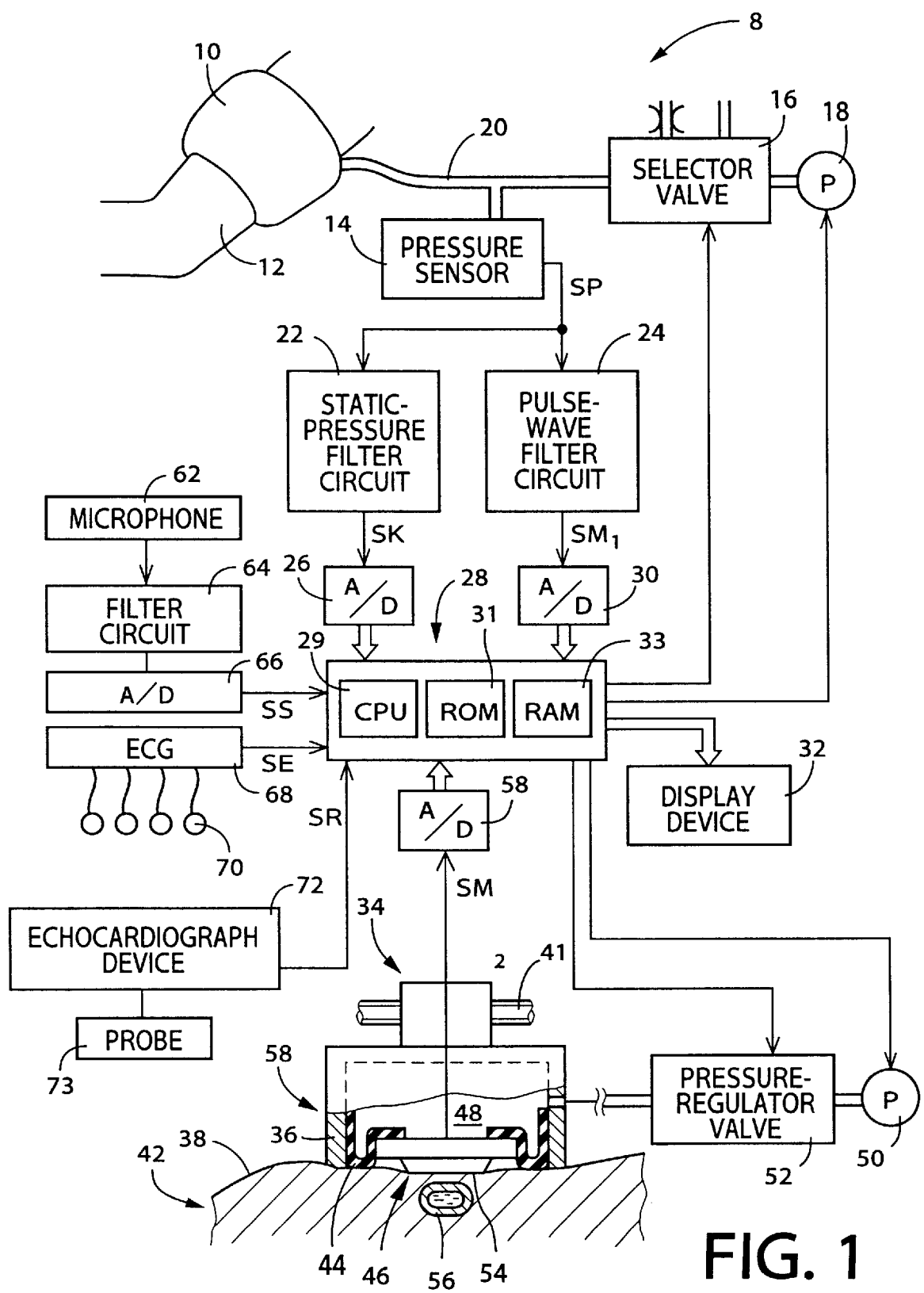
FIG. 1 is a diagrammatic view for explaining the construction of a heart-function monitor apparatus to which the present invention is applied.

Referring first to FIG. 1, there is shown a heart-function monitor apparatus 8 embodying the present invention.

In FIG. 1, reference numeral 10 designates an inflatable cuff which is provided by a belt-like cloth bag and a rubber bag accommodated in the cloth bag. The cuff 10 is worn on a patient by being wound around, for example, an upper arm 12 of a right hand of the patient. A pressure sensor 14, a selector valve 16, and an air pump 18 are connected to the cuff 10 via a piping 20.

The selector valve 16 is selectively placed in an INFLATION position, a SLOW-DEFLATION position, and a QUICK-DEFLATION position. In the INFLATION position, the selector valve 16 permits pressurized air to be supplied from the air pump 18 to the cuff 10; in the SLOW-DEFLATION position, the valve 16 permits the pressurized air to be slowly discharged from the cuff 10 into the atmosphere; and in the QUICK-DEFLATION position, the valve 16 permits the pressurized air to be quickly discharged from the cuff 10 into the atmosphere.

The pressure sensor 14 detects an air pressure in the cuff 10, and supplies a pressure signal, SP, representing the detected pressure, to a static-pressure filter circuit 22 and a pulse-wave fitter circuit 24. The static-pressure filter circuit 22 includes a low-pass filter and transmits, as a cuff-pressure signal SK, a static ("DC") component of the signal SP. The cuff pressure signal SK represents a static pressure, P, of the cuff 10 (hereinafter, referred to simply as the "cuff pressure P"). The cuff-pressure signal SK is supplied to a control device 28 via an analog-to-digital (A/D) converter 26. The pulse-wave filter circuit 24 includes a band-pass filter and transmits, as a pulse-wave signal $SM_1$, an oscillating ("AC") component of the signal SP. The pulse-wave signal $SM_1$ is supplied to the control device 28 via an A/D converter 30. The pulse-wave signal $SM_1$ represents a pulse wave, i.e., an oscillatory pressure wave which is produced from a brachial artery (not shown) of the patient in synchronism with the heartbeat of the patient and is transmitted to the cuff 10 via a skin tissue positioned between the artery and the cuff 10. Thus, the pulse-wave filter circuit 24 serves as a pulse-wave sensor which detects a pulse wave from a body portion of a living subject.

The control device 28 is provided by a microcomputer which includes a central processing unit (CPU) 29, a read only memory (ROM) 31, a random access memory (RAM) 33, and an input and output (I/O) port (not shown). The CPU 29 processes input signals according to control programs pre-stored in the ROM 31 by utilizing a temporary-storage function of the RAM 33, and outputs drive signals to the selector valve 16 and the air pump 18 via the I/O port and respective drive circuits (not shown) so as to regulate the cuff pressure P. In addition, the CPU 29 of the control device 28 operates for determining, according to well-known oscillometric method, blood pressure ("BP") values (e.g., systolic and diastolic BP values; referred to as the "proper BP values" if appropriate) of the patient, based on the variation of respective amplitudes of heartbeat-synchronous pulses of the pulse wave represented by the pulse-wave signal $SM_1$ obtained while the cuff pressure P is decreased slowly at a rate of about 3 mmHg/sec after the cuff pressure P is quickly increased up to a predetermined target pressure. The control device 28 commands a display device 32 including a cathode ray tube (CRT), to indicate the thus determined BP values on the CRT. The control device 28 repeats this BP measurement using the cuff 10, at predetermined intervals of time.

As shown in FIG. 1, the present monitor apparatus further includes a pulse-wave detector probe 34. The detector probe 34 includes an outer (case (not shown) which accommodates a container-like sensor housing 36 and which is detachably attached to a body surface 38 of a wrist 42 of a left hand of the patient with a pair of bands (not shown) which are fastened around the wrist 42. Thus, the wrist 42 is opposite to the upper arm 12 around which the cuff 10 is wound. The outer case support a feed screw 41 which is threadedly engaged with a projection of the sensor housing 36 and which is driven or rotated by an electric motor (not shown) to move the housing 36 in opposite directions intersecting a radial artery 56. With the outer case being attached to the body surface 38 with the help of the bands, an open end of the housing 36 contacts the body surface 38 of the wrist 42.

A pulse-wave sensor 46 is supported by the sensor housing 36 via an elastic diaphragm 44, such that the pulse-wave sensor 46 is displaceable relative to the housing 36, when the diaphragm 44 is inflated, so as to be advanceable out of the open end of the housing 36. The housing 36, the diaphragm 44 and the pulse wave sensor 46 cooperate with one other to define a pressure chamber 48, to which pressurized air is supplied from an air pump 50 via a pressure-regulator valve 52. Thus, the pulse-wave sensor 46 is pressed against the body surface 38 with a pressing force corresponding to the air pressure in the pressure chamber 48. As far as the present embodiment is concerned, the pressing force applied to the pulse-wave sensor 46 is expressed in terms of the air pressure (unit: mmHg) in the pressure chamber 48.

The sensor housing 36 and the elastic diaphragm 44 cooperate with each other to provide a pressing device 58 which presses the pulse-wave sensor 46 against the radial artery 56 via the skin tissue; and the feed screw 41 and the electric motor (not shown) cooperate with each other to provide a pressing-position changing device or a sensor moving device which moves the pulse-wave sensor 46 in the direction intersecting the radial artery 56 and thereby changes the pressing position where the sensor 46 presses the artery 56.

The pulse-wave sensor 46 includes a plurality of semiconductor pressure-sensing elements (not shown) which are provided in a plane surface of a semiconductor substrate, such as a monocrystalline silicon. The plane surface provides a press surface 54 of the pulse-wave sensor 46. The pressure-sensing elements are arranged, in the press surface 54, at small intervals of distance (e.g., 0.2 mm) in a direction parallel to the feed screw 41, that is, the direction in which the sensor 46 is moved by the screw 41. The pulse-wave sensor 46 is pressed on the body surface 38 of the wrist 42 such that the array of pressure-sensing elements cross over, or intersect, the radial artery 56. Thus, each of the pressure-sensing elements of the pulse-wave sensor 46 detects a pressure pulse wave, i.e., an oscillatory pressure wave which is produced from the radial artery 56 in synchronism with the heartbeat of the patient and is transmitted to the body surface 38 or the press surface 54, and produces a pulse-wave signal, $SM_2$, representing the detected pulse wave. The respective pulse-wave signals $SM_2$ produced by the pressure-sensing elements of the pulse-wave sensor 46 are supplied to the control device 28 via an A/D converter 58.

The control device 28 operates, according to the control programs pre-stored in the ROM 31, for supplying drive signals to the air pump 50 and the pressure-regulator valve 52 via respective drive circuits (not shown), so as to regulate the air pressure in the pressure chamber 48. When the control device 28 operates for carrying out, for example, a BP-monitor operation, the control device 28 collects, while slowly changing (e.g., increasing) the pressure in the chamber 48, the pulse-wave signals $SM_2$ supplied from the individual pressure-sensing elements of the pulse-wave sensor 46. Based on the thus collected pulse-wave signals $SM_2$, the control device 28 determines an optimum air pressure (i.e., optimum pressing force), $P_{HDPO}$, to be applied to the pulse-wave sensor 46, by identifying an air pressure value in the chamber 48 at the time when a portion of the wall of the radial artery 56 is partly flattened under the pressing force of the pulse-wave sensor 46. Since the manner of determination of the optimum pressing force is well known in the art, no more description is provided.

Based on the collected pulse-wave signals $SM_2$, the control device 28 additionally selects an optimum pressure-sensing element located right above the center of the radial artery 56, by identifying one of the pressure-sensing elements of the pulse wave sensor 46 that provides a pulse wave signal $SM_2$ having the greatest amplitude of the respective amplitudes provided by all the pressure-sensing elements. Thus, the control device 28 controls the pressure regulator valve 52 so as to maintain the pressure of the chamber 48 at the determined optimum air pressure $P_{HDPO}$, and receives the pulse-wave signal $SM_2$ from the selected optimum pressure-sensing element with the chamber 48 being maintained at the optimum air pressure $P_{HDPO}$. It is speculated that, since the optimum pressure-sensing element is located right above the center of the artery 56, the pulse-wave signal $SM_2$ supplied from the optimum element is free of the influence due to the elastic or tensile force produced in the wall of the artery 56 and accordingly accurately represents BP in the artery 56. That is, the waveform of the pulse-wave signal $SM_2$ supplied from the optimum pressure-sensing element accurately indicates the instantaneous variation of BP of the patient.

Figure 2:
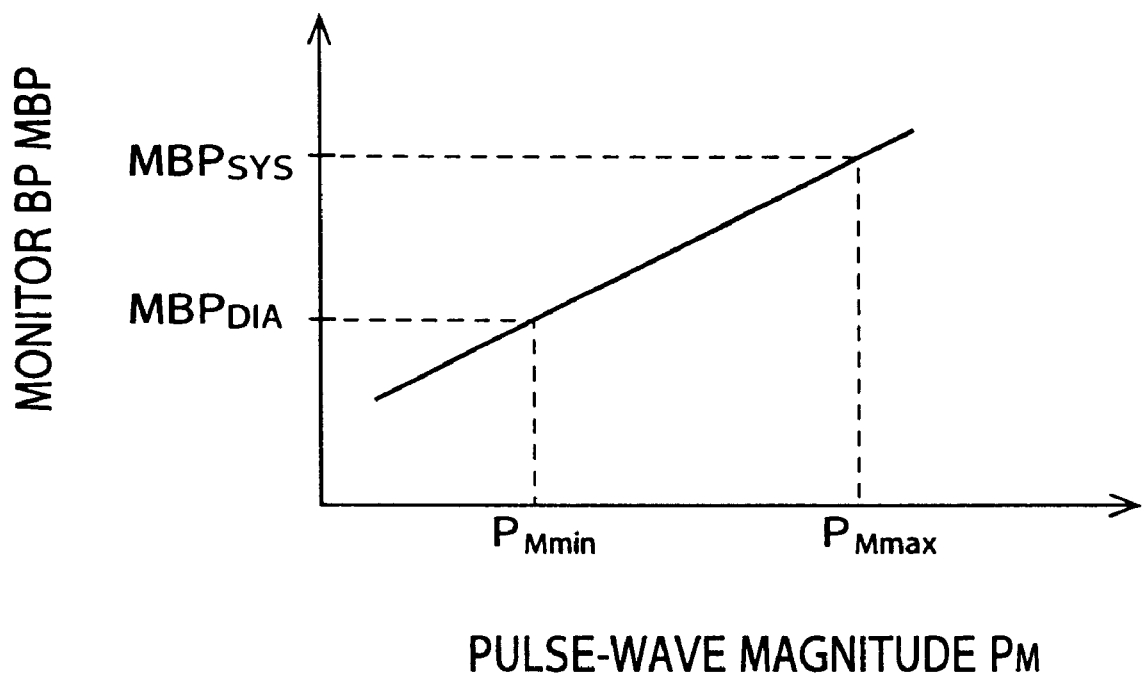
FIG. 2 is a graph representing a relationship between blood pressure ("BP") and pulse-wave magnitude, which is used by the apparatus of FIG. 1 to estimate an arterial-BP waveform based on a pressure pulse wave detected by a pressure-pulse-wave sensor of the apparatus.

In addition, each time a systolic and a diastolic BP values, $BP_{SYS}$, $BP_{DIA}$, are measured using the cuff 10, the control device 28 operates, according to the control programs pre-stored in the ROM 31, for determining a relationship between blood pressure and pulse wave magnitude (referred to as the "MBP–$P_M$ relationship"), as shown in FIG. 2, based on the measured systolic and diastolic BP values $BP_{SYS}$, $BP_{DIA}$ and a maximum and a minimum magnitude (i.e., upper-peak and lower-peak magnitudes), $P_{Mmax}$, $P_{Mmin}$, of one heartbeat-synchronous pulse of the pulse-wave signal $SM_2$ supplied from the pulse-wave sensor 416 (i.e., the optimum pressure-sensing element thereof). The difference between the maximum and minimum magnitudes $P_{Mmax}$, $P_{Mmin}$ of each heartbeat-synchronous pulse is defined as the amplitude of the each pulse. According to the thus determined MBP–$P_M$ relationship, the control device 28 successively or continuously determines a systolic and a diastolic BP value, $MBP_{SYS}$, $MBP_{DIA}$, (i.e., estimated or monitor BP values) of the patient, based on a maximum and a minimum magnitude $P_{Mmax}$, $P_{Mmin}$ of each of respective heartbeat-synchronous pulses of the pulse-wave signal $SM_2$ detected after the MBP–$P_M$ relationship is determined, and commands the display device 32 to display continuously the monitor BP values $MBP_{SYS}$, $MBP_{DIA}$, in digits, that are determined for the each of the successive heartbeat-synchronous pulses. In addition, the control device 28 commands the display device 32 to display continuously a waveform of the pulse-wave signal $SM_2$ supplied from the optimum pressure-sensing element. This waveform indicates the monitor BP values MBP thus determined for the each successive pulse.

The MBP–$P_M$ relationship shown in FIG. 2 is defined by the following expression (1):

$$MBP = A \cdot P_M + B \quad (1)$$

where

A is a constant representing a slope, and
B is a constant representing an intercept.

Figure 5:
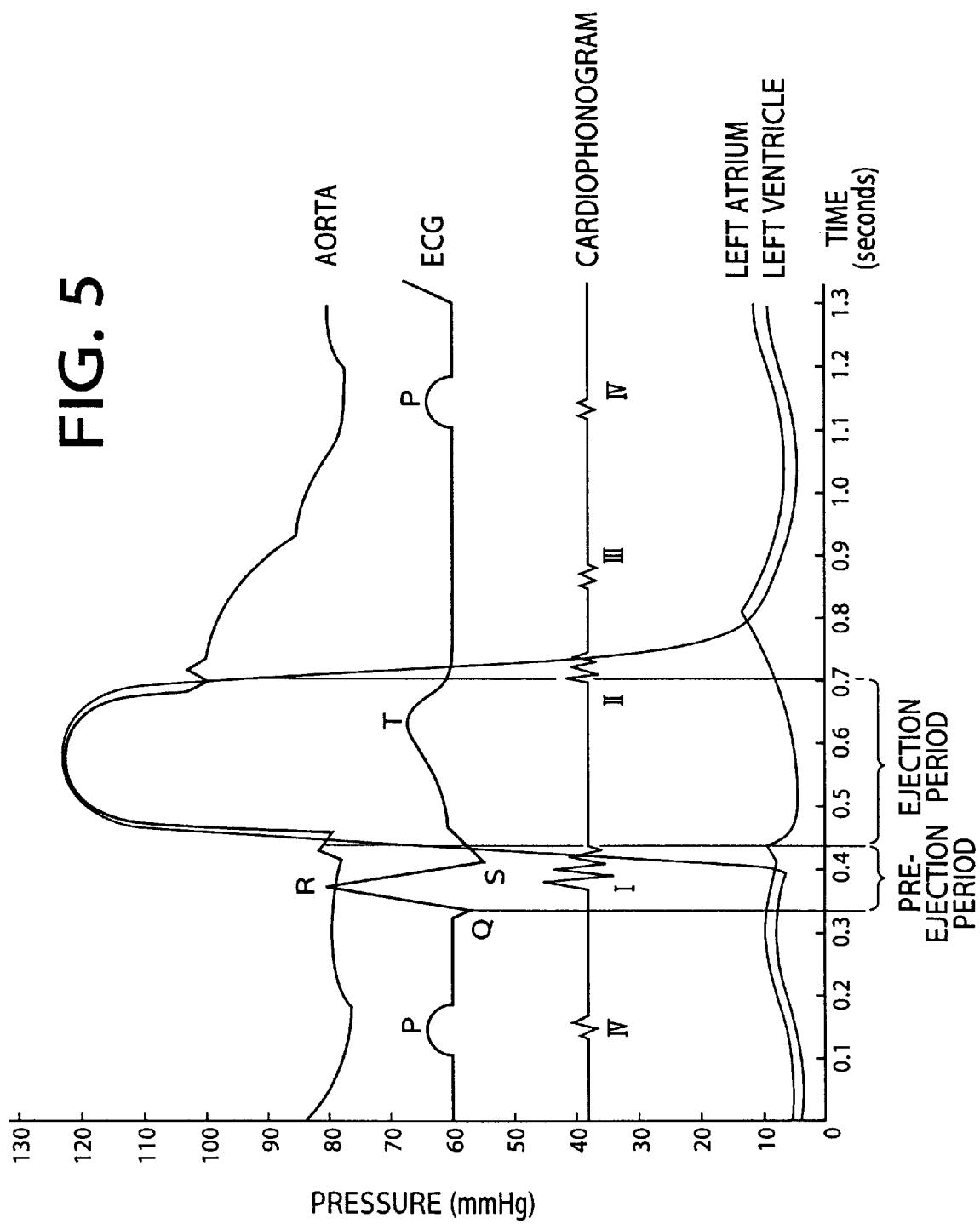
FIG. 5 is a time chart representing a relationship between a pre-ejection period and an ejection period respectively determined by a pre-ejection-period determining means and an ejection-period determining means of the apparatus of FIG. 1, and an aortic-BP waveform, an electrocardiograph ("ECG") waveform, and a cardiophonogram obtained by the apparatus.

In FIG. 1, a heart-sound microphone 62 which functions as a heart-sound sensor is provided in the vicinity of the heart of the patient so as to detect heart sounds produced from the heart, and produces a heart-sound signal, SS, representing the detected heart sounds. The microphone 62 may be worn on a body surface of the patient, but it is preferred that the microphone 62 be provided in a body cavity of the patient, such as the esophagus. The heart-sound signal SS produced by the microphone 62 is supplied to the control device 28 via an amplifier (not shown), a band-pass filter 64 for removing noise from the signal SS, and an A/D converter 66. The heart sounds represented by the heart-sound signal SS include, as shown in FIG. 5, a first sound I corresponding to the closing of the mitral valve and the opening of the aortic valve, and a second sound II corresponding to the closing of the aortic valve.

An electrocardiograph ("ECG") device 68 includes a plurality of electrodes 70 which are adhered to a body surface of the patient such that the adhered electrodes 70 surround the heart of the patient, detects, through the adhered electrodes 70, an electrocardiogram ("ECG") waveform induced by the heart, and produces an ECG signal, SE, representing the detected ECG waveform. The ECG signal SE is supplied to the control device 28. Each period or cycle of the ECG signal SE includes, as shown in FIG. 5, well-known P wave, Q wave, R wave, S wave and T wave in this order.

An echocardiograph device 72 includes a probe 73 adapted to be worn on a chest of the patient, and non-invasively measures, in a method known as M-mode echocardiography or UCG (ultrasonic cardiography), a simultaneous inner volume of the left ventricle of the heart. The probe 73 has an incorporated oscillator (not shown) for emitting an ultrasonic wave of 1 to 10 MHz, and detects respective waves (echoes) reflected by two walls of the left ventricle that are opposed to each other to define the left ventricle in the direction of emission of the wave, and produces an echo signal, SR, representing the detected echoes. The echo signal SR is supplied to the control device 28. The control device 28 continuously detects, based on the echo signal SR supplied from the device 72, respective simultaneous motions of the walls of the left ventricle. More specifically described, the control device 28 calculates, based on the echo signal SR, a simultaneous distance between the two walls of the left ventricle. In addition, the control device 28 calculates, according to a predetermined relationship (i.e., mathematical formula or expression) between left-ventricle volume and left-ventricle wall distance, a left-ventricle telesystolic volume, $V_{es}$, based on the minimum distance between the two walls during each cycle corresponding to each beat of the heart, and additionally calculates, according to the same relationship, a left-ventricle telediastolic volume, $V_{ed}$, based on the maximum distance between the two walls during each cycle. Moreover, the control device 28 calculates, based on the left-ventricle telesystolic and telediastolic volumes $V_{es}$, $V_{ed}$, a stroke volume SV and an output rate, EF, of the left ventricle of the heart. The output rate EF is obtained by dividing the stroke volume SV by the telediastolic volume $V_{ed}$.

The control device 28 processes the ECG signal SE, the heart-sound signal SS and the pulse-wave signal $SM_2$ so as to calculate a telediastolic aortic BP value, $P_{ad}$, a telesystolic aortic BP value, $P_{es}$, a pre-ejection period, PEP, and an ejection time or period, ET, and calculates, based on the thus calculated values $P_{ad}$, $P_{es}$, PEP, ET, the stroke volume SV, the output rate EF, and a non-invasively estimated left-ventricle telediastolic pressure, $P_{ed}$, i.e., a left-ventricle inner pressure at a telediastolic time of the heart, a left-ventricle telesystolic elastance $E_{es}$, according to the following expression (2):

$$E_{es}=[P_{ad}+\{(P_{ad}-P_{ed})/PEP\}\times ET\times\alpha_0-P_{es}]/SV \quad (2)$$

The left-ventricle telesystolic elastance $E_{es}$ is calculated for each of successive heartbeat-synchronous pulses of the pulse-wave signal $SM_2$, and is stored in a memory device (not shown) such as a hard disk, a semiconductor memory card, or a magnetic tape. The control device 28 controls the display device 32 or a printer (not shown) to display or print a timewise trend or change of the thus determined telesystolic elastance values $E_{es}$.

Figure 3:
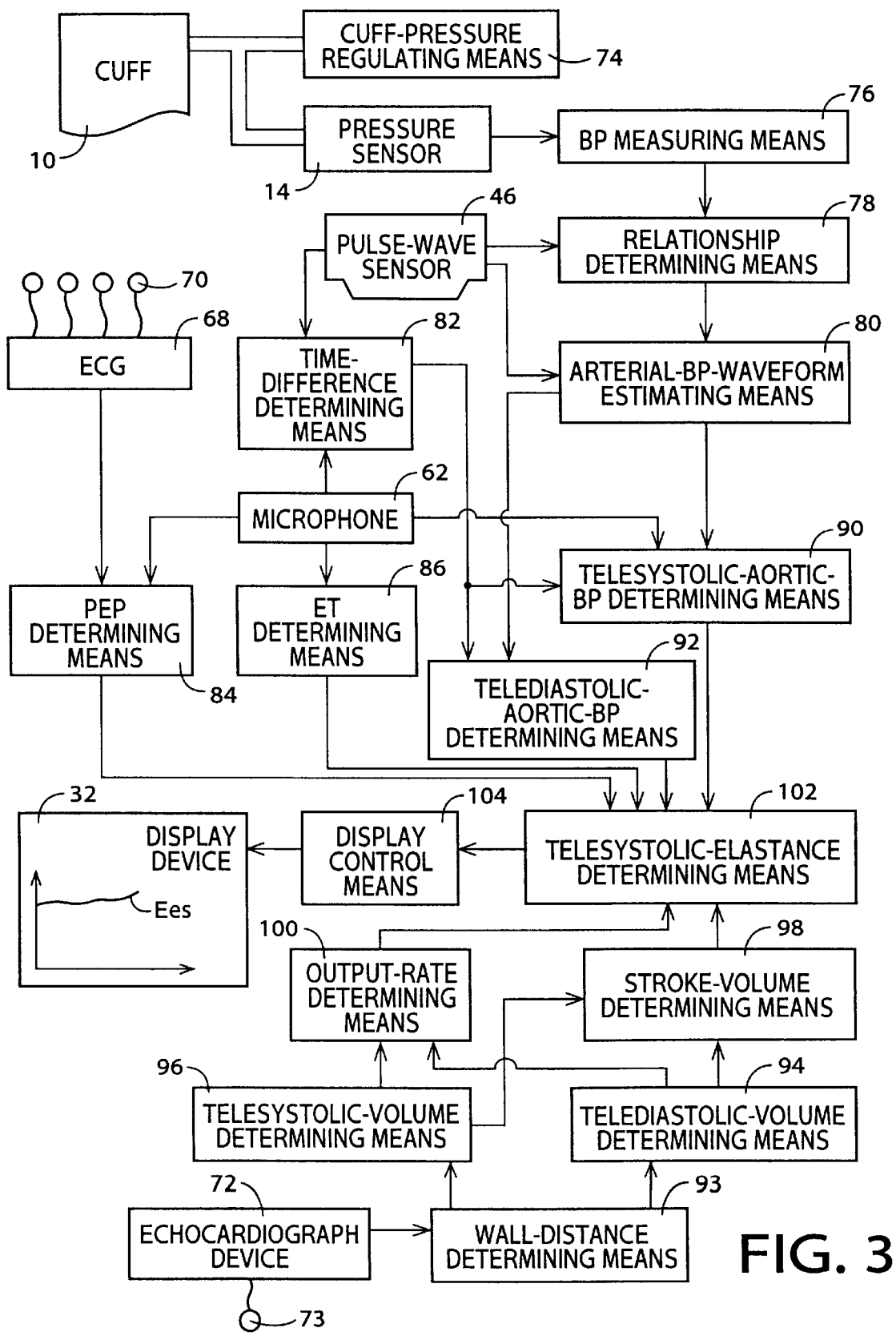
FIG. 3 is a diagrammatic view for explaining important control functions of a control device of the apparatus of FIG. 1.

FIG. 3 shows important control functions of the control device 28. In a BP measuring operation, the pressure sensor 14 detects the pressing pressure of the inflatable cuff 10 that is changed by a cuff-pressure regulating means 74. A BP measuring means 76 measures, according to the oscillometric method or the Korotkoff-sound method, a systolic BP value $BP_{SYS}$, a mean BP value $BP_{MEAN}$, and a diastolic BP value $BP_{DIA}$ (i.e., proper BP values) of the patient, based on the change of the pulse-wave signal $SM_1$ (e.g, the change of respective amplitudes of heartbeat-synchronous pulses of the signal $SM_1$), or the change of Korotkoff sounds (e.g., the first and last detection of the sounds) that are obtained while the pressing pressure of the cuff 10 is changed slowly at the rate of about 2 to 3 mmHg/sec by the cuff-pressure regulating means 74.

A relationship determining means 78 determines, in advance, a MBP–$P_M$ relationship, shown in FIG. 2, between blood pressure BP and pulse-wave magnitude $P_M$, based on the pulse-wave signal $SM_2$ detected by the above-indicated optimum pressure-sensing element (hereinafter, referred to as the "active element") of the pulse-wave sensor 46 and the BP values measured by the BP measuring means 76.

Figure 4:
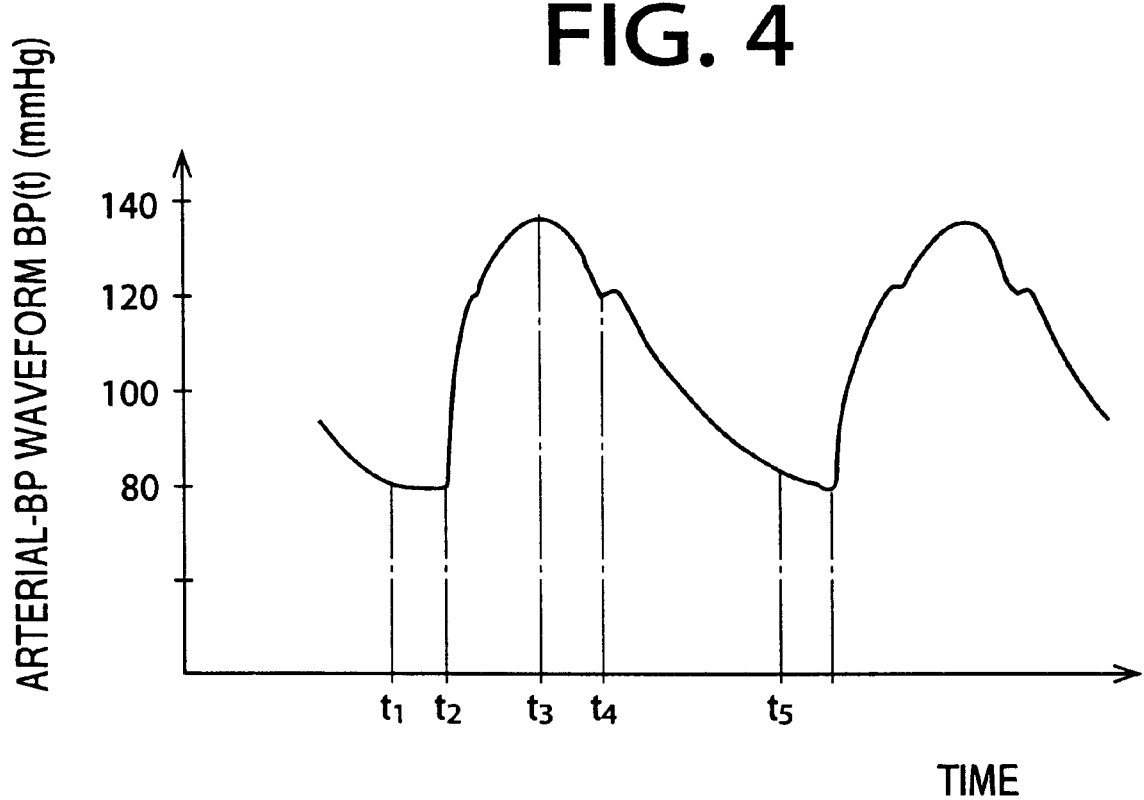
FIG. 4 is a graph representing an arterial-BP waveform estimated by an arterial-BP-waveform estimating means of the apparatus of FIG. 1.

An estimated-BP determining means (or an arterial-BP-waveform estimating means) 80 continuously determines, according to the MBP–$P_M$ relationship shown in FIG. 2, estimated or monitor BP values of the patient based on at least one magnitude of each of successive heartbeat-synchronous pulses of the pulse-wave signal $SM_2$ detected by the above-indicated active element of the pulse-wave sensor 46, and outputs an arterial-BP waveform, BP(t), as shown in FIG. 4, which represents the estimated or monitor BP values of the patient. This arterial-BP waveform BP(t) indicates the waveform of BP of the brachial artery of the patient, but corresponds to that of the aorta of the patient. Therefore, the arterial-BP-waveform estimating means 80 functions as an estimated-aortic-BP determining means, and the arterial-BP waveform BP(t) represents estimated aortic BP values. In the case, however, where an aortic-BP waveform cannot be estimated by the brachial-artery-BP waveform BP(t) for some reasons, a predetermined transfer function may be employed to determine an aortic-BP waveform based on the brachial-artery-BP waveform BP(t).

A time-difference determining means 82 determines a time difference, TD, between the end of the first sound I detected by the heart-sound microphone 62 and the rising point (i.e., minimum or lower-peak point) of a corresponding heartbeat-synchronous pulse of the pulse-wave signal $SM_2$ detected by the pulse-wave sensor 46. Since the end of the first sound I indicates the time when the left ventricle of the heart starts ejecting blood into the aorta, the time difference TD is equal to a time needed for the aortic BP to propagate from the aorta to the radial artery 56 against which the sensor 46 is pressed. The case where it is difficult to specify the end of the first heart sound I, the first sound T may be replaced by the Q wave, R wave, or S wave of the ECG waveform each of which indicates the time when the heart-ventricle muscle starts excitation, that is, the left ventricle starts contraction.

A PEP determining means 84 non-invasively determines a pre-ejection period PEP between the start of contraction of the cardiac muscle of the left ventricle and the start of ejection of blood from the left ventricle. For example, the PEP determining means 84 determines, for each of successive heartbeat-synchronous pulses of the heart, the pre-ejection period PEP (seconds) by counting reference clock pulses from the time when the Q wave of the ECG waveform is detected to the time when the end of the first sound I is detected. Alternatively, the PEP determining means 84 may determine the pre-ejection period PEP by subtracting the time difference TD determined by the means 82, from a time between the time when the Q wave of the ECG waveform is detected and the time when the rising point of the aortic-BP waveform is detected. In the case where the time difference between the Q wave and the R wave of the ECG waveform can be neglected, the Q wave may be replaced with the R wave that is more easily detected. Since the pre-ejection period PEP is, as shown in the time chart of FIG. 5, the time between the time when the cardiac muscle of the left ventricle of the heart starts contraction and the time when the left ventricle starts outputting blood, i.e., the aortic valve opens, the period PFT is called as an isovolumetric contraction period or time.

An ET determining means 86 non-invasively determines an ejection period ET during which the left ventricle of the heart outputs blood. For example, the ET determining means 86 determines, for each of successive heartbeat-synchronous pulses of the heart, the ejection period ET (seconds) by counting reference clock pulses from the time when the end of the first heart sound I is detected to the time when the start of the second heart sound II is detected. Alternatively, the ET determining means 86 may determine the ejection period ET by first measuring a time period from the Q wave of the ECG waveform is detected to the time when the start of the second sound II is detected, so as to determine the sum, (PEP+ET), of the pre-ejection period PEP and the ejection period ET, that is, a time period during which the heart contracts, and then subtracting, from the sum (PEP+ET), the pre-ejection period PEP determined by the means 84. In this case, too, the R wave may be used in place of the Q wave. Otherwise, the ET determining means 86 may determine the ejection period ET by measuring a time period from the time ($t_2$ in FIG. 4) when the rising point of each heartbeat-synchronous pulse of the estimated arterial-BP waveform BP(t) to the time ($t_4$) when the notch of the each pulse that corresponds to the time when the aortic valve is closed.

A telesystolic-aortic-BP determining means 90 determines a telesystolic-aortic-BP ("TSA-BP") value, $P_{es}$, that is, a BP value in the aorta at the end of the contraction of the left ventricle, based on the estimated arterial-BP waveform BP(t) provided by the means 80, the time difference TD determined by the means 82, and the heart-sound signal SS detected by the microphone 62. For example, since the start of the second heart sound II is detected when the aortic valve is closed, that is, when the contraction of the left ventricle ends, and the aortic BP at the start of the second sound II propagates to the radial artery 56 after the time difference TD, the start of the second sound II is identified, and a UP value corresponding to a magnitude taken or indicated by the estimated arterial-BP waveform BP(t) at a time after the time difference TD from the time when the start of the second sound II is identified, is determined as the TSA-BP value $P_{es}$.

A telediastolic-aortic-BP determining means 92 determines a telediastolic-aortic-BP ("TDA-BP") value, $P_{ad}$, that is, a BP value in the aorta at the end of the expansion of the heart, based on the estimated arterial-BP waveform BP(t) provided by the means 80. For example, a BP value corresponding to a magnitude taken or indicated by the estimated arterial-BP waveform BP(t) at a time after the time difference TD from the time when the Q wave of the ECG waveform that corresponds to the start of contraction of the cardiac muscle, that is, the end of expansion of the same is detected, is determined as the TDA-BP value $P_{ad}$.

A wall-distance determining means 93 determines, based on the echo signal SR supplied from the echocardiograph device 72, the respective motions of the two walls that define the left ventricle in the direction of emission of the ultrasonic wave from the device 72, and continuously calculates an instantaneous distance, DL, between the two walls during each cycle corresponding to each beat of the heart.

A telediastolic-volume determining means 94 determines, according to the predetermined expression between left-ventricle volume V and left-ventricle wall distance DL, a left-ventricle telediastolic volume $V_{ed}$ based on the greatest or maximum distance, $DL_{max}$, between the two walls during each cycle corresponding to each beat of the heart. The maximum distance $DL_{max}$ is determined by the wall-distance determining means 93.

A telesystolic-volume determining means 96 determines, according to the same predetermined expression, a left-ventricle telesystolic volume $V_{es}$ based on the smallest or minimum distance, $DL_{min}$, between the two walls during each cycle corresponding to each beat of the heart. The minimum distance $DL_{min}$ is determined by the wall-distance determining means 93.

A stroke-volume determining means 98 non-invasively estimates or determines a stroke volume SV, i.e., a volume of the blood outputted or ejected by one beat of the left ventricle. The stroke-volume estimating means 98 determines, as the stroke volume SV, the difference, ($V_{ed}$-$V_{es}$), between the left-ventricle telediastolic volume $V_{ed}$ determined by the means 94 an the left-ventricle telesystolic volume $V_{es}$ determined by the means 96.

An output-rate determining means 100 determines an output rate EF of the left ventricle by dividing the stroke volume SV by the left-ventricle telediastolic volume $V_{ed}$ determined by the means 94.

An elastance determining means 102 determines, according to a predetermined relationship, e.g., the relationship defined by the above-indicated expression (2), a left-ventricle telesystolic elastance $E_{es}$, based on the pre-ejection period PEP determined by the means 84 in each cycle corresponding to each beat of the heart, the ejection period ET determined by the means 86 in the each cycle, the TSA-BP value $P_{es}$ determined by the means 90 in the each cycle, the TDA-BP value $P_{ad}$ determined by the means 92 in the each cycle, the stroke volume SV determined by the means 98 in the each cycle, and a non-invasively estimated left-ventricle telediastolic pressure $P_{ed}$. The elastance determining means 102 outputs the left-ventricle telesystolic elastance $E_{es}$ determined in each cycle corresponding to each beat of the heart, or a moving average of a predetermined number of elastance values $E_{es}$ determined in the predetermined number of successive cycles corresponding to the predetermined number of successive beats of the heart. The predetermined number may be, e.g., five.

The ratio or coefficient $\alpha_0$ occurring to the expression (2) may be obtained according to the following expression (3) or (4):

$$\alpha_0 = C_1 + C_2 \times EXP(C_3 \times EF) \qquad (3)$$

where $C_1$, $C_2$, and $C_3$ are constants which are experimentally obtained.

$$\alpha_0 = C_4 + C_5 \times EXP(C_6 \times EF) + C_7 \times EXP\{C_8 \times PEP/(PEP+ET)\} \qquad (4)$$

where $C_4$, $C_5$, $C_6$, $C_7$, and $C_8$ are constants which are experimentally obtained.

In the expressions (3), (4), EXP(Z) is an exponential function of Z. The base of EXP(Z) may be the base of natural logarithm. For example, the constants $C_1$, $C_2$, and $C_3$ may be -0.771, 0.864, and 0.929, respectively, and the constants $C_4$, $C_5$, $C_6$, $C_7$, and $C_8$ may be -0.366, 0.484, 1.426, -2.185, and -20.692, respectively.

Thus, in the case where the coefficient $\alpha_0$ is obtained according to the expression (3) or (4), the left-ventricle telesystolic elastance $E_{es}$ is calculated based on the output rate EF determined by the means 100, as well.

The above-indicated left-ventricle telediastolic pressure $P_{ed}$ is a left-ventricle inner pressure at the time when contraction of the left ventricle starts. The heart-function monitor apparatus 8 includes a left-ventricle-pressure determining or estimating means which non-invasively and continuously determines or estimates an inner pressure of the left ventricle of the heart. Thus, the left-ventricle-pressure determining means determines the left-ventricle telediastolic pressure $P_{ed}$. The telediastolic left-ventricle pressure $P_{ed}$ is about 10 mmHg that is sufficiently lower than the telediastolic aorta pressure $P_{ad}$ of about 70 to 90 mmHg, and does not influence so much the telesystolic left-ventricle elastance $E_{es}$ determined according to the expression (2). Therefore, a constant value which is experimentally determined in advance may be used as the telediastolic pressure $P_{ed}$.

Here, the expression (2) is described in detail. A relationship between an inner volume V of the left ventricle of the heart and an inner pressure P of the same may be expressed in a two-dimensional coordinate system, shown in FIG. 6, which has a pressure axis and a volume axis. A pressure-volume loop representing each beat cycle of the heart has a generally rectangular shape including an isovolumetric expansion line, $L_3$, an equal-pressure expansion line, $L_4$, an isovoltimetric contraction line, $L_5$, and an equal-pressure contraction line, $L_6$. In the coordinate system, a symbol, $V_0$, indicates a left-ventricle unstressed volume that is an inner volume of the left ventricle at the time when the inner pressure of the same is zero. The left-ventricle unstressed volume $V_0$ is, as shown in FIG. 7, the intersection point of the volume axis and a telesystolic pressure-volume line, $L_{es}$, that is a line representing a relationship between the left-ventricle volume V and the end point of the equal-pressure contraction that is the intersection point of the two lines $L_3$, $L_6$.

Figure 6:
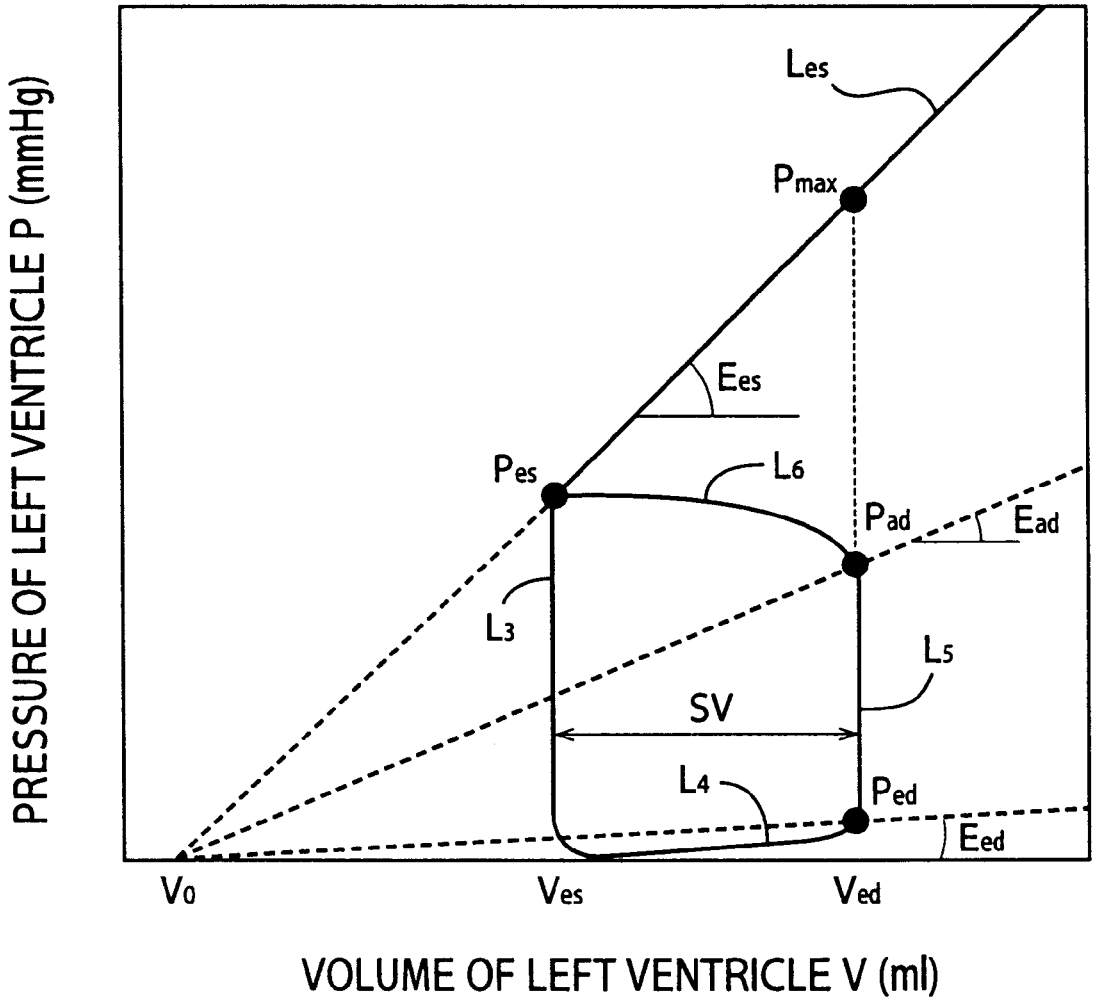
FIG. 6 is a graph showing a one-pulse pressure-volume loop representing a relationship between an inner volume and an inner pressure of the left ventricle of a living subject.
Figure 7:
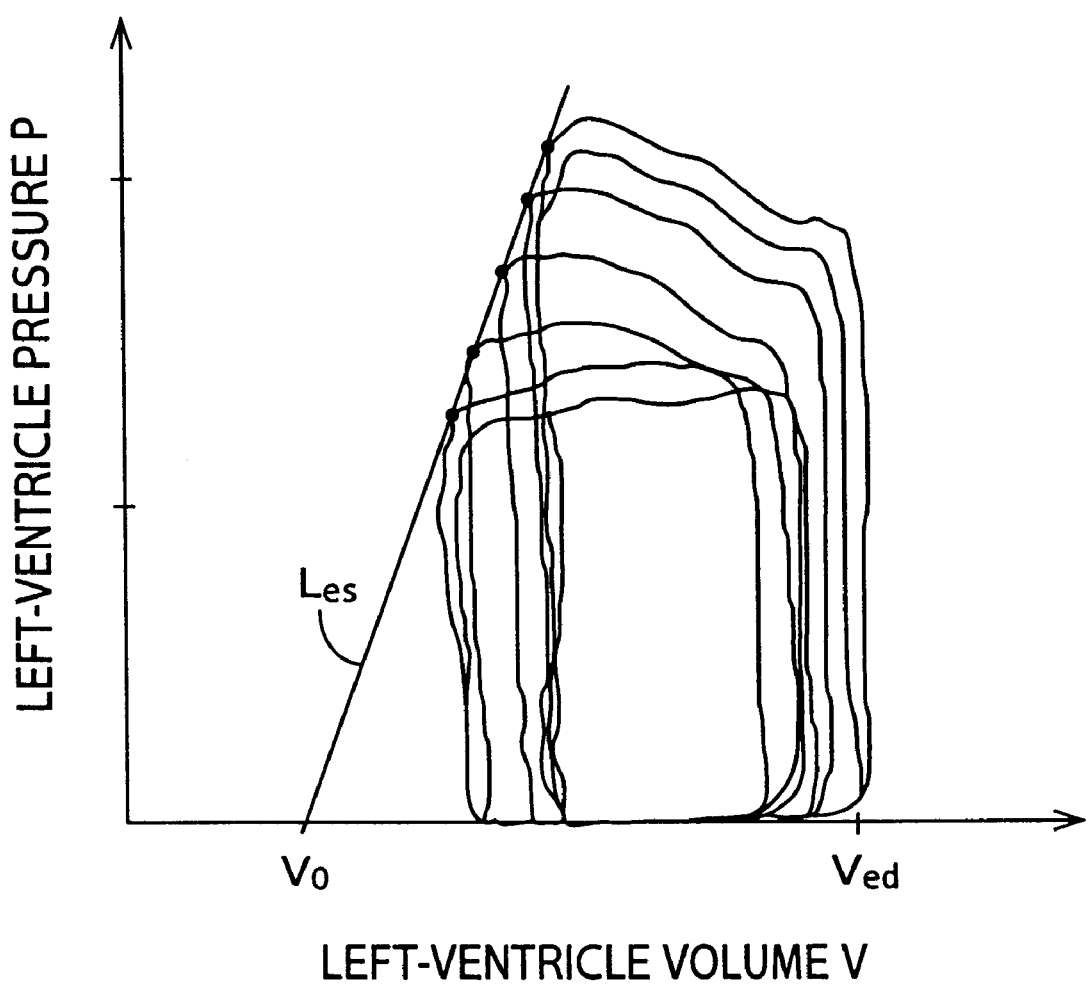
FIG. 7 is a graph for explaining a relationship between a plurality of pressure-volume loops and a telesystolic pressure-volume line, $L_{es}$.

On the generally rectangular, pressure-volume loop shown in FIG. 6, an elastance, E(t), is obtained by dividing the continuously obtained inner pressure P(t) of the left ventricle by the difference, (V(t)-$V_0$), of the inner volume V(t) of the left ventricle and the left-ventricle unstressed volume $V_0$. Thus, the elastance E(t) is also called as a pressure-volume ratio. Therefore, the left-ventricle telesystolic elastance $E_{es}$ is defined as the pressure-volume ratio at the telesystolic time of the heart, that is, the slope of the telesystolic pressure-volume line $L_{es}$. A width of the pressure-volume loop in a direction along the volume axis indicates the stroke volume SV, i.e., the volume of blood outputted during each beat cycle of the heart.

Figure 8:
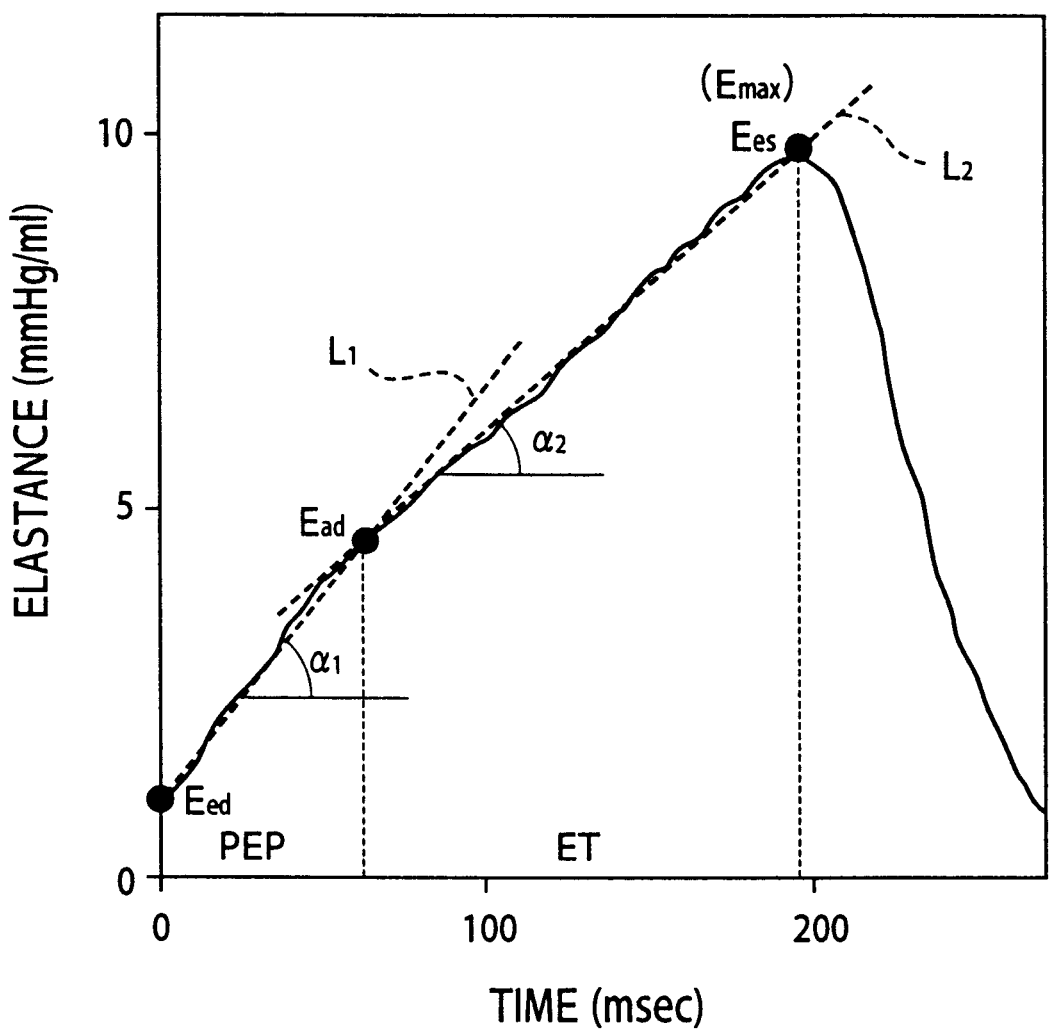
FIG. 8 is a graph showing a curve representing a relationship between elastance (i.e., pressure-volume ratio) and time, which corresponds to the one-pulse pressure-volume loop of FIG. 6.

FIG. 8 shows a two-dimensional coordinate system having an axis of ordinate representing the elastance E(t) continuously calculated from the pressure-volume loop shown in FIG. 6, and an axis of abscissa representing time, t. Thus, FIG. 8 shows a curve of the elastance E(t) that corresponds to one beat cycle of the heart, i.e., one heartbeat-synchronous pulse. FIG. 8 shows two straight lines, $L_1$, $L_2$ that approximates a first half portion of the pressure-volume-ratio curve between its start end and a maximum pressure-volume ratio $E_{max}$, i.e., a left-ventricle telesystolic elastance $E_{es}$. The first straight line $L_1$ approximates a portion of the curve that corresponds to the pre-ejection period PEP, and connects between an elastance $E_{ed}$ at the start of the pre-ejection period PEP and an elastance $E_{ad}$ at the end of the pre-ejection period PEP. The second straight line $L_2$ approximates another portion of the curve that corresponds to the ejection period ET, and connects between the elastance $E_{ad}$ at the start of the ejection period ET, i.e., at the end of the pre-ejection period PEP and the elastance $E_{es}$ at the end of the ejection period ET, i.e., at the telesystolic time.

Since the coefficient "$\alpha_0$" of the expression (2) is the ratio of a slope $\alpha_2$ of the straight line $L_2$ to a slope $\alpha_1$ of the straight line $L_1$, the coefficient "$\alpha_0$" is defined by the following expression (5):

$$\alpha_0 = \alpha_2/\alpha_1 = \{(E_{es}-E_{ad}) \times PEP\}/\{(E_{ad}-E_{ed}) \times ET\} \quad (5)$$

The left-ventricle telesystolic elastance $E_{es}$ is defined by the following expression (6), by re-arranging the expression (5):

$$E_{es} = E_{ad} + \{(E_{ad}-E_{ed})/PEP\} \times ET \times \alpha_0 \quad (6)$$

From the pressure-volume loop shown in FIG. 6, the following expressions (7) to (10):

$$P_{ad} = E_{ad} \times (V_{ed}-V_0) \quad (7)$$

$$P_{ed} = E_{ed} \times (V_{ed}-V_0) \quad (8)$$

$$P_{max} = E_{es} \times (V_{ed}-V_0) \quad (9)$$

$$E_{es} = (P_{max}-P_{es})/SV \quad (10)$$

The maximum pressure $P_{max}$ is an estimated pressure which would be taken if no blood were ejected from the left ventricle, that is, a left-ventricle inner pressure at the intersection point of the telesystolic pressure-volume line $L_{es}$ and the isovolumetric contraction line $L_5$.

When $E_{ad}$, $E_{ed}$, $E_{es}$ defined by re-arranging the expressions (7), (8), (9) are substituted for $E_{ad}$, $E_{ed}$, and $E_{es}$ occurring to the expression (6), the following expression (11) is obtained:

$$P_{max} = P_{ad} \times \{(P_{ad}-P_{ed})/PEP\} \times ET \times \alpha_0 \quad (11)$$

When $P_{max}$ defined by the expression (11) is substituted for $P_{max}$ occurring to the expression (10), the above-indicated expression (2) is obtained.

The above-indicated expressions (3), (4) each used for determining the coefficient $\alpha_0$ occurring to the expression (2), are obtained based on the experimental fact that the left-ventricle telesystolic elastance $E_{es}$ is strongly related to the output rate EF and a cardiac contraction index, $I_V$. The coefficients, $C_1$ to $C_8$, occurring to the expressions (3), (4) are obtained by well-known regression calculations based on ratio values $\alpha_0$, output rate values EF, pre-ejection period values PEP, and ejection period values ET which are experimentally obtained.

Figure 9:
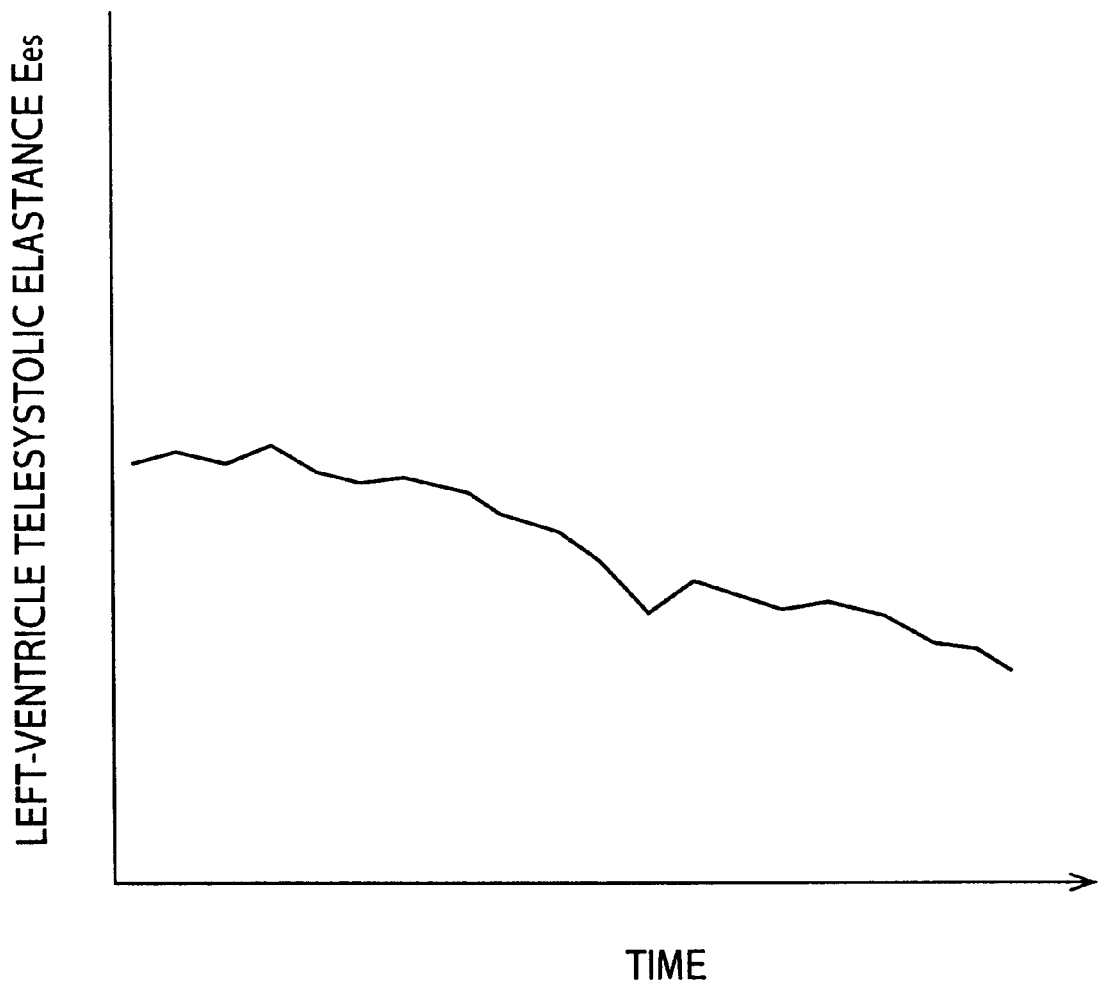
FIG. 9 is a graph showing a timewise trend or change of left-ventricle telesystolic elastance values $E_{es}$ that is displayed on a display device of the apparatus of FIG. 1.

Back to FIG. 3, a display control means 104 controls the display device 32 to display a timewise trend or change of the left-ventricle telesystolic elastance values $E_{es}$ continuously determined by the means 102, as shown in FIG. 9. In the present embodiment, a greater value $E_{es}$ indicates a higher function of the heart of the patient. Therefore, an observer such as a doctor a nurse can monitor the cardiac function of the patient by observing the timewise change (e.g., an abrupt decrease) of the elastance values $E_{es}$ displayed on the display device 32.

Figure 10:
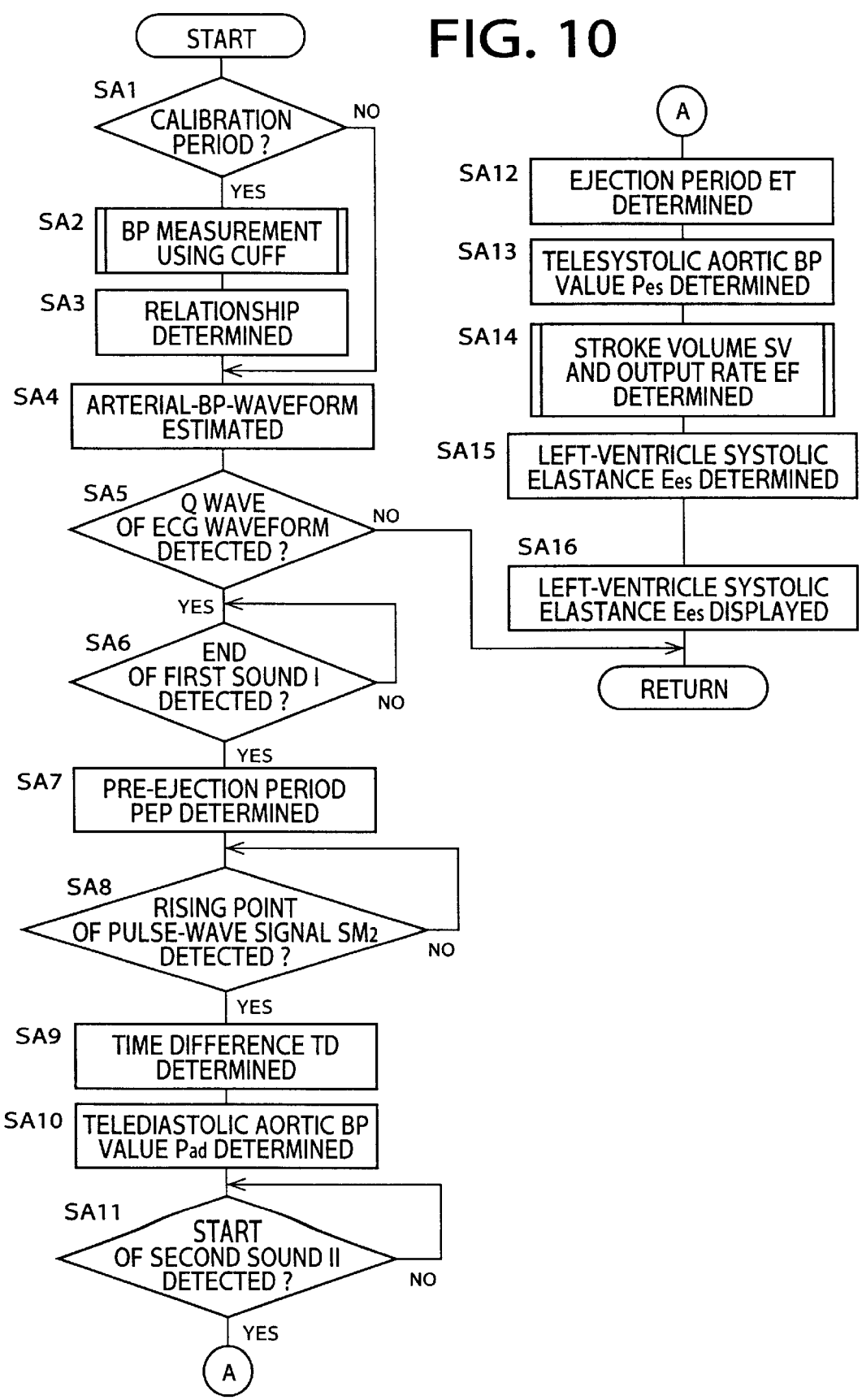
FIG. 10 is a flow chart representing a main routine of a control program according to which the control device of FIG. 3 is operated.

Hereinafter, there will be described the operation of the present heart-function monitor apparatus 8 by reference to the flow chart of FIGS. 10 and 11. FIG. 10 shows a main routine according to which the control device 28 is operated to operate the monitor apparatus 8, and FIG. 11 shows a stroke-volume and output-rate calculating routine as a step of the main routine of FIG. 10.

First, at Step SA1 of FIG. 10, the control device 28 judges whether a predetermined calibration period (e.g., twenty minutes) has elapsed. If a negative judgment is made at Step SA1, the control of the control device 28 skips Step SA2 and SA3 and proceeds with Step SA4 to estimate an arterial-BP waveform. On the other hand, if a positive judgment is made at Step SA1, the control goes to Step SA2 corresponding to the BP measuring means 76. At Step SA2, the control device 28 carries out a BP measuring operation using the inflatable cuff 10, according to the oscillometric method or the Korotkoff-sound method. Step SA2 is followed by Step SA3 corresponding to the relationship determining means 78. At Step SA3, the control device 28 determines a relationship, shown in FIG. 2, based on the BP values BP measured using the cuff 10 by the BP measuring means 76 and the magnitudes $P_M$ of the pressure pulse wave represented by the pulse-wave signal $SM_2$ detected by the active element of the pulse-wave sensor 46.

Step SA3 is followed by Step SA4 corresponding to the arterial-BP-waveform estimating means 80. At Step SA4, the control device 28 converts, according to the relationship determined at Step SA3, the pulse-wave signal $SM_2$ detected by the active element of the pulse-wave sensor 46, into the estimated arterial-BP waveform BP(t), shown in FIG. 4, that represents estimated BP values of the patient.

Step SA4 is followed by Step SA5 to judge whether the Q wave of the ECG waveform represented by the ECG signal SE has been detected. If a negative judgment is made at Step SA5, the present control cycle is ended, and the next control cycle is started. On the other hand, if a positive judgment is made at Step SA, the control goes to Step SA6 to judge whether the end of the first heart sound I represented by the heart-sound signal SS has been detected. If a negative judgment is made at Step SA6, the control device 28 repeats Step SA6. Meanwhile, if a positive judgment is made at Step SA6, the control goes to Step SA7 to determine, as the pre-ejection period PEP, a time period from the time of detection of the Q wave to the time of detection of the end of the first sound I. Thus, Steps SA5 to SA7 correspond to the PEP determining means 84.

At the following step, Step SA8, the control device 28 judges, based on the pulse-wave signal $SM_2$ supplied from the pulse-wave sensor 46, whether the rising point of one heartbeat-synchronous pulse of the estimated arterial-BP waveform BP(t) has been detected. If a negative judgment is made at Step SA8, the control device 28 repeats Step SA8.

Meanwhile, if a positive judgment is made at Step SA8, the control goes to Step SA9 corresponding to the time-difference determining means 82. At Step SA9, the control device 28 determines a time difference TD between the time when the end of the first sound I is detected at Step SA6 and the time when the rising point of the pulse-wave signal $SM_2$ is detected at Step SA8. This time difference TD means a propagation time needed for the blood ejected from the left ventricle of the heart to reach the radial artery 56 against which the pulse-wave sensor 46 is pressed.

At the following step, Step SA10 corresponding to the telediastolic-aortic-BP determining means 92, the control device 28 determines, as the telediastolic aortic BP value $P_{ad}$, a BP value corresponding to a magnitude taken by the estimated arterial-BP waveform BP(t) at a time after the time difference TD determined at Step SA9 from the time when the Q wave of the ECG waveform is detected at Step SA5.

Step SA10 is followed by Step SA11 to judge whether the start of the second sound II represented by the heart-sound signal SS has been detected. The second sound II is produced when the the inner pressure of the left ventricle becomes not higher than that of the aorta and accordingly the aortic valve is closed. Therefore, the start of the second sound II means the end of contraction of the left ventricle, i.e., the telesystolic time. If a negative judgment is made at Step SA11, the control device 28 repeats Step SA11. Meanwhile, if a positive judgment is made at Step SA11, the control goes to Step SA12 to determine, as the ejection period ET during which the blood is ejected from the left ventricle, a time period from the time when the end of the firs sound I is detected at Step SA6 to the time when the start of the second sound II is detected at Step SA11. Thus, Steps SA6, SA11, and SA12 correspond to the ET determining means 86.

At the following step, Step SA13 corresponding to the telesystolic-aortic-BP determining means 90, the control device 28 determines, as the telesystolic aortic BP value $P_{es}$, a BP value corresponding to a magnitude taken by the estimated arterial-BP waveform BP(t) at a time after the time difference TD determined at Step SA9 from the time when the start of the second sound II is detected at Step SA11.

At the following step, Step SA14 corresponding to the stroke-volume determining means 98 and the output-rate determining means 100. At Step SA14, the control device 28 iteratively calculates a stroke volume SV and an output rate EF, according to the subroutine of FIG. 11, at a considerably short period, thereby updating the stroke volume SV and the output rate EF.

At Step SB1 of FIG. 11, the echocardiograph device 72 detects the ultrasonic waves generated by the oscillator incorporated by the probe 73 thereof and then reflected by the walls of the left ventricle, and supplies the echo signal SR representing the detected ultrasonic waves to the control device 28. The control device 28 judges whether it has received the echo signal SR. If a negative judgment is made at Step SB1, this routine is ended and repeated. Meanwhile, if a positive judgment is made, the control of the control device 28 goes to Step SB2 corresponding to the wall-distance determining means 93. At Step SB2, the control device 28 measures the respective motions of the two walls of the left ventricle that are opposed to each other in the direction of generation of the ultrasonic wave, and determines an instantaneous distance DL of the two walls of the left ventricle.

At the following step, Step SB3, the control device 28 judges, based on the echo signal SR, whether it has detected a length of the echo signal that corresponds to one cycle corresponding to one beat of the heart. If a negative judgment is made at Step SB3, this routine is ended and repeated. Meanwhile, if a positive judgment is made, it means that the control device 28 has continuously determined a batch of instantaneous distances DL corresponding to the one beat of the heart. Hence, the control of the control device 28 goes to Step SB4 corresponding to the left-ventricle telediastolic volume determining means 94. At Step SB4, the control device 28 determines or selects, from the batch of instantaneous distances DL collected at Step SB3, the greatest or maximum distance $DL_{max}$ of the two walls during the one cycle corresponding to the one beat. The maximum wall distance $DL_{max}$ corresponds to the maximum volume of the left ventricle during the one cycle. In addition, the control device 28 determines, based on the maximum wall distance $DL_{max}$, a left-ventricle telediastolic volume $V_{ed}$ according to the predetermined mathematical expression defining the predetermined relationship between left-ventricle volume and left-ventricle wall distance.

At the following step, Step SB5, corresponding to the left-ventricle telesystolic volume determining means 96, the control device 28 determines or selects, from the batch of instantaneous distances DL collected at Step SB3, the smallest or minimum distance $DL_{min}$ of the two walls during the one cycle corresponding to the one beat. The minimum wall distance $DL_{min}$ corresponds to the minimum volume of the left ventricle during the one cycle. In addition, the control device 28 determines, based on the minimum wall distance $DL_{min}$, a left-ventricle telesystolic volume $V_{es}$ according to the same predetermined mathematical expression as employed at Step SB4.

At the following step, Step SB6, corresponding to the stroke-volume determining means 98, the control device 28 estimates the difference ($V_{ed}-V_{es}$) of the left-ventricle telediastolic volume $V_{ed}$ determined at Step SB4 and the left-ventricle telesystolic volume $V_{es}$ determined at Step SB5, as the stroke volume SV that is the volume of the blood outputted or ejected from the left ventricle during the one beat of the heart.

At the following step, Step SB7, corresponding to the output-rate determining means 100, the control device 28 non-invasively determines the output rate EF of the left ventricle by dividing the stroke volume SV determined at Step SB6, by the left-ventricle telediastolic volume $V_{ed}$ determined at Step SB4.

Back to Step SA15 corresponding to the left-ventricle telesystolic elastance determining means 102, the control device 28 determines, according to the second and fourth expressions (2) and (4), a left-ventricle telesystolic elastance $E_{es}$ based on the pre-ejection period PEP determined at Step SA10, the ejection period ET determined at Step SA12, the aorta telediastolic pressure $P_{ad}$ determined at Step SA10, the aorta telesystolic pressure $P_{es}$ determined at Step SA13, the stroke volume SV determined at Step SB6 (Step SA14), the output rate EF determined at Step SB7 (Step SA14), and the left-ventricle telediastolic pressure $P_{ed}$ predetermined as a constant value, e.g., 10 mmHg.

At the following step, Step SA16 corresponding to the display control means 104, the control device 28 controls the display device 32 to display, in digits, the left-ventricle telesystolic elastance value $E_{es}$ determined for the one beat of the heart at Step SA15, and additionally display a trend graph, as shown in FIG. 9, representing a timewise change of the continuously determined elastance values $E_{es}$.

It emerges from the foregoing description that the left-ventricle telesystolic elastance determining means 102 (Step SA15) determines, according to the predetermined relationship defined by the second expression (2), the left-ventricle telesystolic elastance $E_{es}$ based on the pre-ejection period PEP, the ejection period ET, the aorta telediastolic pressure $P_{ad}$, the aorta telesystolic pressure $P_{es}$, and the stroke volume SV all of which are non-invasively measured or determined, and the left-ventricle telediastolic pressure $P_{ed}$ predetermined as the constant value. Thus, the present monitor apparatus 8 can non-invasively, easily, and continuously monitor the left-ventricle telesystolic elastance $E_{es}$ indicating the cardiac function of the patient.

In the illustrated embodiment, the output-rate determining means 100 (Step SB7) determines the output rate EF that is known to be closely related to the left-ventricle telesystolic elastance $E_{es}$, and the left-ventricle telesystolic elastance determining means 102 (Step SA15) determines the coefficient $\alpha_0$ occurring to the second expression (2), based on the output rate EF determined by the means 100, and the ventricle contraction index $I_V$ that is conventionally known as an index of the contracting ability of the heart. Therefore, the present monitor apparatus 8 can more accurately determine the telesystolic elastance $E_{es}$.

In the illustrated embodiment, the heart-sound microphone 62 is located in the body cavity such as the esophagus in the vicinity of the heart, so as to detect the first and second heart sounds I, II produced from the heart, and the PEP determining means 84 (Steps S5 to S7) determines, as the pre-ejection period PEP, a time period from the time when the Q wave of the ECG waveform is detected through the ECG 68 to the time when the end of the first heart sound I is detected through the microphone 62. Thus, this means 84 can non-invasively and accurately measure the pre-ejection period PEP.

The present heart-function monitor apparatus 8 employs the display control means 104 (Step SA16) which controls the display device 32 to display the left-ventricle telesystolic elastance values $E_{es}$ continuously determined by the means 102 (Step SA15), along the time axis, as shown in FIG. 9. For example, in the case where the cardiac function of a patient who is undergoing a surgical operation is lowering, the present apparatus 8 can display a timewise change of the left-ventricle telesystolic elastance values $E_{es}$ that accurately reflects the lowering of the cardiac function. Thus, a medical staff such as a doctor or a nurse can estimate an abnormality of the cardiac function before the elastance $E_{es}$ actually indicates an abnormal value.

While the present invention has been described in its preferred embodiments, it is to he understood that the invention may otherwise be embodied.

For example, in the illustrated embodiment, the telesystolic-aorta-BP determining means 90 determines, as the telesystolic aorta BP value $P_{es}$, a magnitude of the estimated arterial-BP waveform BP(t) at a time after the time difference TD from the time when the start of the second heart sound II is detected. The start of the second heart sound II may be replaced by the end of the T wave of the ECG waveform, as shown in FIG. 5. In addition, since the telesystolic aorta BP value $P_{es}$ can be approximated by a mean BP value (i.e., mean arterial pressure), MAP, according to a rule of thumb, an average of instantaneous BP values corresponding to one cycle or period, T, of the estimated arterial-BP waveform BP(t), that is, a mean BP value MAP may be used as the telesystolic aorta BP value $P_{es}$. Since the mean BP value MAP is defined as $\Sigma BP(t)/T$, it can be expressed by a BP value corresponding to a center of gravity of an area enveloped of the one cycle T of the estimated arterial-BP waveform BP(t).

In the illustrated embodiment, the telediastolic-aorta-BP determining means 92 determines, as the telediastolic aorta BP value $P_{ad}$, a magnitude of the estimated arterial-BP waveform BP(t) at a time after the time difference TD from the time when the Q wave of the ECG waveform is detected. However, since the aortic pressure at the telediastolic time of the heart does not change so largely for a considerably long time, as shown in FIG. 5, the estimated arterial-BP waveform BP(t) can be used to estimate an aortic pressure at an arbitrary point during a time period when the first sound I is detected, or an aortic pressure at the time when the R wave or S wave of the ECG waveform is detected, and determine the thus estimated aortic pressure as the telediastolic aorta BP value $P_{ad}$. Alternatively, a BP value corresponding to the rising point of each heartbeat-synchronous pulse of the estimated arterial-BP waveform BP(t) can be used as the telediastolic aorta BP value $P_{ad}$.

In the illustrated embodiment, the coefficient $\alpha_0$ occurring to the second expression (2) is determined according to the third or fourth expression (3) or (4). However, the coefficient $\alpha_0$ may be experimentally determined as a constant value. In the latter case, the degree of accuracy of the left-ventricle telesystolic elastance values $E_{es}$ determined is not so high as that of the values $E_{es}$ determined in the illustrated embodiment, but can be practically used.

In the illustrated embodiment, the stroke-volume determining means 98 determines the stroke volume SV based on the echo signal SR detected by the echocardiograph device 72. However, the control device 28 may estimate, based on the arterial-BP waveform BP(t), shown in FIG. 4, determined by the arterial-BP-waveform determining means 80, a stroke volume SV according to the following expression (12) known as Warnner & Gardner's formula:

$$SV = K\left[\int_{t_3}^{t_4} BPdt - \int_{t_1}^{t_2} BPdt\right]^{1/2} \left\{1 + \frac{\int_{t_1}^{t_3}(BP-20)dt}{\int_{t_3}^{t_5}(BP-20)dt}\right\}$$

In the arterial-BP waveform BP(t) shown in FIG. 4 and the above expression (12), the time $t_1$ of the start of the pre-ejection period PEP is prior by, e.g., 80 milliseconds to the time $t_2$ of the lower peak and the time $t_4$ of the end of the ejection period ET is subsequent by, e.g., 80 milliseconds to the time $t_3$ of the upper peak. In the expression (12), the coefficient, K, is a correcting constant which is calibrated in advance by a value directly obtained by the thermodilusion method.

Alternatively, the stroke-volume determining means 98 may be adapted to determine, according to a predetermined relationship employed in the Kubicek method, a stroke volume SV based on an impedance cardiogram detected by using electrodes worn on neck and waist of a person.

It is to be understood that the present invention may be embodied with other changes, improvements and modifications that may occur to those skilled in the art without departing from the scope and spirit of the invention defined in the appended claims.

What is claimed is:

1. An apparatus for monitoring a function of a heart of a living subject, comprising:
    a pre-ejection period measuring device which non-invasively measures a pre-ejection period from a time when contraction of a cardiac muscle of a left ventricle of the heart starts, to a time when ejection of blood from the left ventricle starts;
    an ejection-period measuring device which non-invasively measures an ejection period during which the blood is ejected from the left ventricle;

an aorta-pressure estimating means for estimating blood pressure values in an aorta of the subject;

a telediastolic-aorta-pressure determining means for determining, based on the aorta blood pressure values estimated by the aorta-pressure estimating means, a telediastolic blood pressure in the aorta at a telediastolic time of the heart;

for determining, based on the aorta blood pressure values estimated by the aorta-pressure estimating means, a telesystolic blood pressure in the aorta at a telesystolic time of the heart;

a stroke-volume measuring device which non-invasively measures a stroke volume that is a volume of blood ejected from the left ventricle of the heart by a one-time beat of the heart; and a telesystolic-elastance determining means for determining, based on the measured pre-ejection period, the measured ejection period, the determined aorta telediastolic blood pressure, the determined aorta telesystolic blood pressure, and the measured stroke volume, a telesystolic elastance of the left ventricle of the heart, according to a predetermined relationship between (A) left-ventricle telesystolic elastance and (B) (b1) pre-ejection period, (b2) ejection period, (b3) aorta telediastolic blood pressure, (b4) aorta telesystolic blood pressure, and (b5) stroke volume.

2. An apparatus according to claim 1, wherein the telesystolic-elastance determining means comprises means for determining, according to said predetermined relationship, the telesystolic elastance of the left ventricle of the heart, based on the measured pre-ejection period, the measured ejection period, the determined aorta telediastolic blood pressure, the determined aorta telesystolic blood pressure, the measured stroke volume, and a predetermined telediastolic pressure in the left ventricle at the telediastolic time of the heart.

3. An apparatus according to claim 2, wherein said predetermined relationship is defined by a following expression:

$$E_e = [P_{ad} + \{(P_{ad} - P_{ed})/PEP\} \times ET \times \alpha_0 - P_{es}]/SV$$

where $E_{es}$ is the left-ventricle telesystolic elastance, $P_{ad}$ is the aorta telediastolic blood pressure, $P_{es}$ is the aorta telesystolic blood pressure, $P_{ed}$ is the left-ventricle telediastolic pressure, ET is the ejection period, PEP is the pre-ejection period, SV is the stroke volume, and $\alpha_0$ is a coefficient.

4. An apparatus according to claim 3, further comprising an output-rate measuring device which non-invasively measures a volume of the left ventricle at the telediastolic time of the heart, and determines an output rate of the left ventricle of the heart by dividing the measured stroke volume by the measured left-ventricle telediastolic volume, wherein the telesystolic-elastance determining means determines, based on the measured pre-ejection period, the measured ejection period, the determined aorta telediastolic blood pressure, the determined aorta telesystolic blood pressure, the measured stroke volume, the measured output rate, and the left-ventricle telediastolic pressure, a telesystolic elastance of the left ventricle of the heart, according a predetermined relationship between (A) left-ventricle telesystolic elastance and (B) (b1) pre-ejection period, (b2) ejection period, (b3) aorta telediastolic blood pressure, (b4) aorta telesystolic blood pressure, (b5) stroke volume, and (b6) output rate.

5. An apparatus according to claim 4, wherein the coefficient $\alpha_0$ of said expression is defined by a following expression:

$$\alpha_0 = C_1 + C_2 + EXP(C_3 \times EF)$$

where

EF is the measured output rate, $C_1$, $C_2$, and $C_3$ are constants which are experimentally obtained, and EXP(Z) is an exponential function of Z.

6. An apparatus according to claim 4, wherein the coefficient $\alpha_0$ of said expression is defined by a following expression:

$$\alpha_0 = C_1 + C_2 \times EXP(C_3 \times EF) + C_4 \times EXP\{C_5 \times PEP/(PEP + ET)\}$$

where

EF is the measured output rate, $C_1$, $C_2$, $C_3$, $C_4$, and $C_5$ are constants which are experimentally obtained, and EXP(Z) is an exponential function of Z.

7. An apparatus according to claim 1, wherein the pre-ejection period measuring device comprises:

an electrocardiograph which includes a plurality of electrodes adapted to contact a body surface of the subject, and which detects, from the subject, an electrocardiogram waveform including a Q wave;

a heart-sound detecting device which is located in a body cavity of the subject, at a position in a vicinity of the heart of the subject, and which detects, from the subject, at least a first heart sound I; and means for determining, as the pre-ejection period, a time period from a time when the Q wave of the electrocardiogram waveform is detected to a time when an end of the first heart sound I is detected.

8. An apparatus according to claim 1, wherein the ejection-period measuring device comprises:

a heart-sound detecting device which is worn on the subject, at a position in a vicinity of the heart of the subject, and which detects, from the subject, a first heart sound I and a second heart sound II; and means for determining, as the ejection period, a time period from a time when an end of the first heart sound I is detected to a time when a start of the second heart sound II is detected.

9. An apparatus according to claim 1, wherein the telediastolic-aorta-pressure determining means comprises:

an electrocardiograph which includes a plurality of electrodes adapted to contact a body surface of the subject, and which detects, from the subject, an electrocardiogram waveform including a Q wave; and means for determining, as the telediastolic aorta blood pressure, a blood pressure which is estimated by the aorta-pressure estimating means as an aorta blood pressure at a time when the Q wave of the electrocardiogram waveform is detected by the electrocardiograph.

10. An apparatus according to claim 1, wherein the telesystolic-aorta-pressure determining means comprises:

a heart-sound detecting device which is worn on the subject, at a position in a vicinity of the heart of the subject, and which detects at least a second heart sound II from the subject; and mean s for determining, as the telesystolic aorta blood pressure, a blood pressure which is estimated by the aorta-pressure estimating means as an aorta blood pressure at a time when a start of the second heart sound II is detected by the heart-sound detecting device.

11. An apparatus according to claim 1, wherein the pre-ejection period measuring device non-invasively measures, each time the heart contracts and expands, a pre-ejection period from a time when the contraction of the cardiac muscle of the left ventricle of the heart starts, to a time when the ejection of the blood from the left ventricle starts; the ejection period measuring device non-invasively measures, each time the heart contracts and expands, an ejection period during which the blood is ejected from the left ventricle starts; the aorta-pressure estimating means estimates, each time the heart contracts and expands, blood pressure values in the aorta of the subject; each time the heart contracts and expands, the telediastolic-aorta-pressure determining means determines, based on the estimated blood pressure values of the aorta, a telediastolic blood pressure in the aorta at a telediastolic time of the heart; each time the heart contracts and expands, the telesystolic-aorta-pressure determining means determines, based on the estimated blood pressure values of the aorta, a telesystolic blood pressure in the aorta at a telesystolic time of the heart; each time the heart contracts and expands, the stroke-volume measuring device measures a stroke volume of the left ventricle; and each time the heart contracts and expands, the telesystolic elastance determining means determines, based on the measured pre-ejection period, the measured ejection period, the determined telediastolic aorta blood pressure, the determined telesystolic aorta blood pressure, and the measured stroke volume, a telesystolic elastance value of the left ventricle of the heart according to said predetermined relationship, and wherein the apparatus further comprises a display device which displays, along an axis indicative of time, the left-ventricle telesystolic elastance values which are successively determined by the telesystolic elastance determining means as the heart successively contracts and expands.

12. An apparatus according to claim 1, wherein the aorta-pressure estimating means comprises:

a blood-pressure measuring device which includes an inflatable cuff adapted to be wound around a body portion of the subject, and which measures at least one blood pressure of the subject when an air pressure in the cuff is changed;

a pulse-wave sensor which is adapted to be pressed against an artery of the subject via a skin tissue of the subject so as to flatten a portion of a wall of the artery, and which detects a pressure pulse wave transmitted thereto from the artery via the flattened wall portion of the artery and the skin tissue;

relationship determining means for determining a relationship between blood pressure and pressure-pulse-wave magnitude, based on at least one blood pressure measured by the blood-pressure measuring device and at least one magnitude of the pressure pulse wave detected by the pulse-wave sensor; and means for calibrating, according to the determined relationship, instantaneous magnitudes of the pressure pulse wave detected by the pulse-wave sensor, and thereby providing a waveform representing the estimated aorta blood pressure values of the subject.

13. An apparatus for monitoring a function of a heart of a living subject, comprising:

a pre-ejection period measuring device which non-invasively measures a pre-ejection period from a time when contraction of a cardiac muscle of a left ventricle of the heart starts, to a time when ejection of blood from the left ventricle starts;

an ejection-period measuring device which non-invasively measures an ejection period during which the blood is ejected from the left ventricle;

an aorta-pressure estimating means for estimating blood pressure values in an aorta of the subject;

a telediastolic-aorta-pressure determining means for determining, based on the aorta blood pressure values estimated by the aorta-pressure estimating means, a telediastolic blood pressure in the aorta at a telediastolic time of the heart;

a telesystolic aorta-pressure determining means for determining, based on the aorta blood pressure values estimated by the aorta-pressure estimating means, a telesystolic blood pressure in the aorta at a telesystolic time of the heart;

a stroke-volume and output-rate measuring device which non-invasively measures a stroke volume that is a volume of blood ejected from the left ventricle of the heart, and an output rate that is a percentage of blood in the left ventricle of the heart ejected from the left ventricle of the heart, by a one-time beat of the heart; and a telesystolic-elastance determining means for determining, based on the measured pre-ejection period, the measured ejection period, the determined aorta telediastolic blood pressure, the determined aorta telesystolic blood pressure, the measured stroke volume and the measured output rate, a telesystolic elastance of the left ventricle of the heart, according to a predetermined relationship between (A) left-ventricle telesystolic elastance and (B) (b1) pre-ejection period, (b2) ejection period, (b3) aorta telediastolic blood pressure, (b4) aorta telesystolic blood pressure, (b5) stroke volume and (b6) output rate.

14. An apparatus according to claim 13, wherein the telesystolic-elastance determining means comprises means for determining, according to said predetermined relationship, the telesystolic elastance of the left ventricle of the heart, based on the measured pre-ejection period, the measured ejection period, the determined aorta telediastolic blood pressure, the determined aorta telesystolic blood pressure, the measured stroke volume and output rate, and a predetermined telediastolic pressure in the left ventricle at the telediastolic time of the heart.

15. An apparatus according to claim 14, wherein said predetermined relationship is defined by a following expression:

$$E_{es}=[P_{ad}+\{(P_{ad}-P_{ed})/PEP\}\times ET \times \alpha_0 - P_{es}]/SV$$

where $E_{es}$ is the left-ventricle telesystolic elastance, $P_{ad}$ is the aorta telediastolic blood pressure, $P_{es}$ is the aorta telesystolic blood pressure, $P_{ed}$ is the left-ventricle telediastolic pressure, ET is the ejection period, PEP is the pre-ejection period, SV is the stroke volume, and $\alpha_0$ is a coefficient.

16. An apparatus according to claim 15, wherein the stroke volume and output-rate measuring device non-invasively measures a volume of the left ventricle at the telediastolic time of the heart, and determines an output rate of the left ventricle of the heart by dividing the measured stroke volume by the measured left-ventricle telediastolic volume, wherein the telesystolic-elastance determining means determines, based on the measured pre-ejection period, the measured ejection period, the determined aorta telediastolic blood pressure, the determined aorta telesystolic blood pressure, the measured stroke volume, the measure output rate, and the left-ventricle telediastolic pressure, a telesystolic elastance of the left ventricle of the heart, according to a predetermined relationship between (A) left-ventricle telesystolic elastance and (B) (b1) pre-ejection period, (b2) ejection period, (b3) aorta telediastolic blood pressure, (b4) aorta telesystolic blood pressure, (b5) stroke volume, and (b6) output rate.

17. An apparatus according to claim 16, wherein the coefficient $\alpha_0$ of said expression is defined by a following expression:

$$\alpha_0 = C_1 + C_2 \times EXP(C_3 \times EF)$$

where

EF is the measured output rate, $C_1$, $C_2$, and $C_3$ are constants which are experimentally obtained, and EXP(Z) is an exponential function of Z.

18. An apparatus according to claim 16, wherein the coefficient $\alpha_0$ of said expression is defined by a following expression:

$$\alpha_0 = C_1 + C_2 \times EXP(C_3 \times EF) + C_4 \times EXP\{C_5 \times PEP/(PEP + ET)\}$$

where

EF is the measured output rate, $C_1$, $C_2$, $C_3$, $C_4$, and $C_5$ are constants which are experimentally obtained, and EXP(Z) is an exponential function of Z.

19. An apparatus according to claim 13, wherein the pre-ejection period measuring device comprises:

an electrocardiograph which includes a plurality of electrodes adapted to contact a body surface of the subject, and which detects, from the subject, an electrocardiogram waveform including a Q wave;

a heart-sound detecting device which is located in a body cavity of the subject, at a position in a vicinity of the heart of the subject, and which detects, from the subject, at least a first heart sound I; and means for determining, as the pre-ejection period, a time period from a time when the Q wave of the electrocardiogram waveform is detected to a time when an end of the first heart sound I is detected.

20. An apparatus according to claim 13, wherein the ejection-period measuring device comprises:

a heart-sound detecting device which is worn on the subject, at a position in a vicinity of the heart of the subject, and which detects, from the subject, a first heart sound I and a second heart sound II; and means for determining, as the ejection period, a time period from a time when an end of the first heart sound I is detected to a time when a start of the second heart sound II is detected.

21. An apparatus according to claim 13, wherein the telediastolic-aorta-pressure determining means comprises:

an electrocardiograph which includes a plurality of electrodes adapted to contact a body surface of the subject, and which detects, from the subject, an electrocardiogram waveform including a Q wave; and means for determining, as the telediastolic aorta blood pressure, a blood pressure which is estimated by the aorta-pressure estimating means as an aorta blood pressure at a time when the Q wave of the electrocardiogram waveform is detected by the electrocardiograph.

22. An apparatus according to claim 13, wherein the telesystolic-aorta-pressure determining means comprises:

a heart-sound detecting device which is worn on the subject, at a position in a vicinity of the heart of the subject, and which detects at least a second heart sound II from the subject; and means for determining, as the telesystolic aorta blood pressure, a blood pressure which is estimated by the aorta-pressure estimating means as an aorta blood pressure at a time when a start of the second heart sound II is detected by the heart-sound detecting device.

23. An apparatus according to claim 13, wherein the pre-ejection period measuring device non-invasively measures, each time the heart contracts and expands, a pre-ejection period from a time when the contraction of the cardiac muscle of the left ventricle of the heart starts, to a time when the ejection of the blood from the left ventricle starts; the ejection period measuring device non-invasively measures, each time the heart contracts and expands, an ejection period during which the blood is ejected from the left ventricle starts; the aorta-pressure estimating means estimates, each time the heart contracts and expands, blood pressure values in the aorta of the subject; each time the heart contracts and expands, the telediastolic-aorta-pressure determining means determines, based on the estimated blood pressure values of the aorta, a telediastolic blood pressure in the aorta at a telediastolic time of the heart; each time the heart contracts and expands, the telesystolic-aorta-pressure determining means determines, based on the estimated blood pressure values of the aorta, a telesystolic blood pressure in the aorta at a telesystolic time of the heart; each time the heart contracts and expands, the stroke-volume and output-rate measuring device measures a stroke volume and a stroke rate of the left ventricle; and each time the heart contracts and expands, the telesystolic elastance determining means determines, based on the measured pre-ejection period, the measured ejection period, the determined telediastolic aorta blood pressure, the determined telesystolic aorta blood pressure, and the measured stroke volume and stroke rate, a telesystolic elastance value of the left ventricle of the heart according to said predetermined relationship, and wherein the apparatus further comprises a display device which displays, along an axis indicative of time, the left-ventricle telesystolic elastance values which are successively determined by the telesystolic elastance determining means as the heart successively contracts and expands.

24. An apparatus according to claim 13, wherein the aorta-pressure estimating means comprises:

a blood-pressure measuring device which includes an inflatable cuff adapted to be wound around a body portion of the subject, and which measures at least one blood pressure of the subject when an air pressure in the cuff is changed;

a pulse-wave sensor which is adapted to be pressed against an artery of the subject via a skin tissue of the subject so as to flatten a portion of a wall of the artery, and which detects a pressure pulse wave transmitted thereto from the artery via the flattened wall portion of the artery and the skin tissue;

relationship determining means for determining a relationship between blood pressure and pressure-pulse-wave magnitude, based on at least one blood pressure measured by the blood-pressure measuring device and at least one magnitude of the pressure pulse wave detected by the pulse-wave sensor; and means for calibrating, according to the determined relationship, instantaneous magnitudes of the pressure pulse wave detected by the pulse-wave sensor, and thereby providing a waveform representing the estimated aorta blood pressure values of the subject.

25. A method for monitoring a function of a heart of a living subject, comprising the steps of:

non-invasively measuring a pre-ejection period from a time when contraction of a cardiac muscle of a left ventricle of the heart starts, to a time when ejection of blood from the left ventricle starts with a pre-ejection period measuring device;

non-invasively measuring an ejection period during which the blood is ejected from the left ventricle with an ejection-period measuring device;

estimating blood pressure values in an aorta of the subject with an aorta-pressure estimating means;

determining, based on the aorta blood pressure values estimated by the aorta-pressure estimating means, a telediastolic blood pressure in the aorta at a telediastolic time of the heart with a telediastolic-aorta-pressure determining means;

determining, based on the aorta blood pressure values estimated by the aorta-pressure estimating means, a telesystolic blood pressure in the aorta at a telesystolic time of the heart with a telesystolic-aorta-pressure determining means;

non-invasively measuring a stroke volume that is a volume of blood ejected from the left ventricle of the heart, and an output rate that is a percentage of blood in the left ventricle of the heart ejected from the left ventricle of the heart, by a one-time beat of the heart with a stroke-volume and output-rate measuring device; and determining, based on the measured pre-ejection period, the measured ejection period, the determined aorta telediastolic blood pressure, the determined aorta telesystolic blood pressure, the measured stroke volume and the measured output rate, a telesystolic elastance of the left ventricle of the heart, according to a predetermined relationship between (A) left-ventricle telesystolic elastance and (B) (b1) pre-ejection period, (b2) ejection period, (b3) aorta telediastolic blood pressure, (b4) aorta telesystolic blood pressure, (b5) stroke volume and (b6) output rate with a telesystolic-elastance determining means.

* * * * *